US 9,388,384 B2

(12) United States Patent
Kim et al.

(10) Patent No.: US 9,388,384 B2
(45) Date of Patent: Jul. 12, 2016

(54) MESENCHYMAL STEM CELLS PRODUCED FROM HUMAN PLURIPOTENT STEM CELLS

(75) Inventors: Hyo Soo Kim, Seoul (KR); Hyun Jae Kang, Seoul (KR); Eun Ju Lee, Seoul (KR); Young Bae Park, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 0 days.

(21) Appl. No.: 13/504,881

(22) PCT Filed: Oct. 28, 2009

(86) PCT No.: PCT/KR2009/006267
§ 371 (c)(1),
(2), (4) Date: Jul. 17, 2012

(87) PCT Pub. No.: WO2011/052818
PCT Pub. Date: May 5, 2011

(65) Prior Publication Data
US 2012/0276625 A1    Nov. 1, 2012

(30) Foreign Application Priority Data
Oct. 27, 2009  (KR) .................. 10-2009-0102458

(51) Int. Cl.
*C12N 5/00* (2006.01)
*C12N 5/0775* (2010.01)
*A61K 35/48* (2015.01)

(52) U.S. Cl.
CPC .............. *C12N 5/0662* (2013.01); *A61K 35/48* (2013.01); *C12N 2500/38* (2013.01); *C12N 2501/105* (2013.01); *C12N 2501/11* (2013.01); *C12N 2501/115* (2013.01); *C12N 2501/155* (2013.01); *C12N 2501/165* (2013.01); *C12N 2501/39* (2013.01); *C12N 2506/02* (2013.01)

(58) Field of Classification Search
CPC .................... C12N 2501/165; C12N 2501/39; C12N 2506/02; C12N 5/0662; C12N 5/00
See application file for complete search history.

(56) References Cited

PUBLICATIONS

Zheng et al (Cell Research, 16: 713-722, 2006).*
Itskovitz-Eldor et al (Molecular Medicine, 6(2): 88-95, 2000).*
Cameron et al, (Biotechnol Bioeng, 94(5): 938-48, 2006).*
Boyd et al, (Tissue Engineering, Part A, 15(8): 1897-1907, 2009.*
"Human Embryonic Stem (ES) Cell Embryoid Body Formation Medium," Millipore, Dec. 2007, 3 pages.
Barberi et al., "Derivation of Multipotent Mesenchymal Precursors from Human Embryonic Stem Cells," *PLoS Medicine* 2(6): 0554-0560, Jun. 2005.
Boyd et al., "Human Embryonic Stem Cell-Derived Mesoderm-like Epithelium Transitions to Mesenchymal Progenitor Cells," *Tissue Engineering: Part A* 15(8):1897-1907, 2009.
Lian et al., "Derivation of Clinically Compliant MSCs from CD105+, CD24- Differentiated Human ESCs," *Stem Cells* 25:425-436, 2007.
Olivier et al., "Differentiation of Human Embryonic Stem Cells into Bipotent Mesenchymal Stem Cells," *Stem Cells* 24:1914-1922, 2006.
Rungarunlert et al., "Embryoid body formation from embryonic and induced pluripotent stem cells: Benefits of bioreactors," *World J Stem Cells* 1(1):11-21, 2009.
Trivedi et al., "Derivation of SSEA4-/CD73+ Mesenchymal Stem Cells from Human Embryonic Stem Cells," *Blood* (ASH Annual Meeting Abstracts) 108: Abstract 2579, 2006.

* cited by examiner

*Primary Examiner* — Deborah Crouch
*Assistant Examiner* — Magdalene Sgagias
(74) *Attorney, Agent, or Firm* — Seed IP Law Group PLLC

(57) ABSTRACT

Provided is a method for producing mesenchymal stem cells from human pluripotent stem cells, the method including: a) forming embryonic bodies from human pluripotent stem cells; b) attaching the embryonic bodies to a culture dish to induce natural differentiation of the embryonic bodies into mesenchymal stem cells; and c) performing continuous proliferative culturing of the mesenchymal stem cells while still maintaining the identity of the mesenchymal stem cells. Also, provided is a standardized method for inducing differentiation of mesenchymal stem cells, which can be broadly applied to all human pluripotent stem cells regardless of a difference in the genetic background thereof. Ultimately, the present invention can continuously mass-produces the mesenchymal stem cells necessary for regenerative medicine and cell therapy by using human pluripotent stem cells, thereby realizing practical uses of cell therapy products, and further the present invention is expected to highly contribute to treatments of incurable diseases, such as cardiovascular diseases and neurological disorders.

2 Claims, 22 Drawing Sheets

Echocardiographic variables in mice cryoinjury model

| | Baseline | | | 4 weeks | | | 8 weeks | |
|---|---|---|---|---|---|---|---|---|
| | LVEDD (mm) | LVFS (%) | | LVEDD (mm) | LVFS (%) | | LVEDD (mm) | LVFS (%) |
| Control | 39.1±3.8 | 22.1±0.2 | | 41.6±3.7 | 20.3±2.9 | | 42.6±4.7 | 20.5±1.0 |
| Cell transplantation | 38.0±0.9 | 22.8±0.4 | | 40.0±1.5 | 25.0±2.2 | | 41.1±2.5 | 23.7±3.7 |

*LVEDD: left ventricular end diastolic dimension, LVFS: left ventricular fractional shortening

FIG. 9D

MESENCHYMAL STEM CELLS PRODUCED FROM HUMAN PLURIPOTENT STEM CELLS

CROSS-REFERENCE TO RELATED APPLICATIONS

This application claims priority from and the benefit of Korean Patent Application No. 10-2009-0102458, filed on Oct. 27, 2009, which is hereby incorporated by reference for all purposes as if fully set forth herein.

BACKGROUND OF THE INVENTION

1. Field of the Invention

The present invention relates to a method for inducing mesenchymal stem cells from human pluripotent stem cells, mesenchymal stem cells produced by the method, and cell therapy products including the mesenchymal stem cells.

2. Discussion of the Background

Stem cells are cells which are capable of differentiating into a variety of cells constituting tissues of an organism, and generally refer to undifferentiated cells before differentiation, which can be obtained from respective tissues of an embryo, a fetus, and an adult body. The stem cells differentiating into specific cells by a differentiation stimulus (environment); allowing proliferation (expansion) thereof by producing the same cells as themselves through cell division (self-renewal), unlike cells of which cell division has been ceased due to completion of differentiation; and having plasticity in differentiation since they can differentiate into other cells under different environments or by different differentiation stimuli.

The stem cells may be classified into pluripotent, multipotent, and unipotent stem cells according to differentiation capability thereof. The pluripotent stem cells are pluripotent cells having totipotency to differentiate into all cells, and these include embryonic stem cells (ES cells), and induced pluripotent stem cells (iPS cells), etc. Adult stem cells may be examples of the multipotent and/or unipotent stem cells.

The embryonic stem S cells are formed from the inner cell mass of blastocyte in early embryogenesis; have totipotency to differentiate into all cells so that they can differentiate into any kind of tissue cells; can be cultured in an immortal and undifferentiated state; can be inherited to the next generation through preparation of germ cells, unlike the adult stem cells (Thomson et al., Science, 282; 1145-1147, 1998; Reubinoff et al., Nat, Biotechnol., 18; 399-404, 2000).

Human embryonic stem cells are prepared by isolating and culturing only the inner cell mass at the time of forming the a human embryo formation and, currently, the human embryonic stem cells prepared globally have been obtained from the frozen embryos remaining after sterilization operations. There have been various attempts to use pluripotent human embryonic stem cells that can differentiate into all cells as a cell therapy product; however, they have not yet completely overcome high barriers such as the risk of carcinogenesis and immunological rejection.

As one complement of these, induced pluripotent stem (iPS) cells have been reported recently. The iPS cells, which are included in the concept of the pluripotent stem cells, are cells obtained by de-differentiating adult cells of which differentiation is ended in several manners and thereby return them to embryonic-like state in an early stage of differentiation. So far, it has been reported that the de-differentiated cells exhibit almost the same characteristics as the embryonic stem cells, which are pluripotent stem cells, in view of gene expression and differentiation capability. These iPS cells can also use autologous cells and thereby exclude the risk of immunological rejection, however the risk of tumorigenesis still remain as a subject to be solved.

Recently, mesenchymal stem cells that have an immunoregulatory function and are free from the risk of tumorigenesis, have been presented as an alternative for solving such problems. The mesenchymal stem cells are multipotent cells which are capable of differentiating into adipocytes, osteocytes, chondrocytes, myocytes, neurocytes, cardiomyocytes, etc., and have been reported to have a function of regulating immune responses. The mesenchymal stem cells can be isolated and cultured from various tissues, but their capacity and cell surface markers are different from one another depending on the origins thereof. Therefore, it is not easy to clearly define the mesenchymal stem cells. However, the mesenchymal stem cells are generally defined by cells which can differentiate into osteocytes, chondrocytes and myocytes; have a spiral form; and express CD73(+), CD105(+), CD34(−), and CD45(−), which are basic cell surface markers.

Meanwhile, the minimal number about $1\times10^9$ of cells required in the fields of regenerative medicine and/or cell therapy needs to be satisfied, in order for the mesenchymal stem cells to be used as cell therapy products. However, the number of cells actually required is further increased, when considering experiments for setting conditions and standards. Therefore, at least 10 passages are needed for an in vitro experiment in order to supply such amount of cells from existing mesenchymal stem cells derived from various origins. In this case, the cells become aged and modified, and thus, they may not be adequate any more for the use as cell therapy products. Although the conditions and standards have been set by using these cells, some problems may occur that the cells might already become depleted before they are actually used in the therapy, so that the mesenchymal stem cells from others need to be used, and in that case, additional experiments need to be carried out due to the use of different cells.

The most ideal alternative to solve the above problems of the existing mesenchymal stem cell culturing system is to use human pluripotent stem cells to produce mesenchymal stem cells. However, so far, the induction of differentiation from human pluripotent stem cells into mesenchymal stem cells had required an induction procedure by a specific cytokine (e.g., BMP, bFGF), which costs much and needs control of concentration, or an induction procedure on xeno feeders (OP9 mouse cell lines) having the risk of xeno pathogen, and a sorting by a specific marker (e.g., CD73), thereafter.

Furthermore, as for the mesenchymal stem cells produced by these methods, it is difficult to maintain its fundamental state and production efficiency is not high. Moreover, human pluripotent stem cells having different genetic backgrounds have different physiological mechanisms, and thus cannot use the existing methods for inducing differentiation of mesenchymal stem cells, which were previously established in specific lines. Therefore, there was some difficulty that in order to induce mesenchymal stem cells from human pluripotent stem cells having different genetic origins, separate differentiation-inducing methods need to be developed and applied. For these reasons, the mesenchymal stem cells have limitations in being used as ideal cell therapy products in the fields of regenerative medicine and cell therapy.

SUMMARY OF THE INVENTION

The present invention provides a mass-production method of mesenchymal stem cells with high efficiency, which is generally applicable to human pluripotent stem cells having various genetic backgrounds. Furthermore, the present invention provides mesenchymal stem cells produced by the method, cell therapy products including the mesenchymal stem cells, and standardized culturing system for producing the mesenchymal stem cells from human pluripotent stem cells.

In order to resolve the above problem, the present invention provides a method for producing mesenchymal stem cells from human pluripotent stem cells, the method includes: a) forming embryonic bodies from human pluripotent stem cells; b) attaching the embryonic bodies to a tissue culture dish and then inducing spontaneous differentiation of the embryonic bodies into mesenchymal stem cells; and c) performing continuous proliferative culture of the mesenchymal stem cells while maintaining the identity of the mesenchymal stem cells. Specifically, the inducing of the differentiation may include inducing spontaneous differentiation by formation of loops of autologous cytokine, and has a characteristic of using a medium comprising human epidermal growth factor (hEGF), vascular endothelial growth factor (VEGF), human fibroblast growth factor-basic (hFGF-B), insulin-like growth factor (IGF-1), hydrocortisone, ascorbic acid, etc. like may be used in order to maintain and proliferatively culture the differentiation-induced mesenchymal stem cells.

BRIEF DESCRIPTION OF THE DRAWINGS

FIG. 9A-D shows the results obtained by observing the function using an ischemic cardiovascular disease mouse model in order to estimate functionality of the mesenchymal stem cells obtained by the method of the present invention;

DETAILED DESCRIPTION OF THE ILLUSTRATED EMBODIMENTS

Figure 1A:
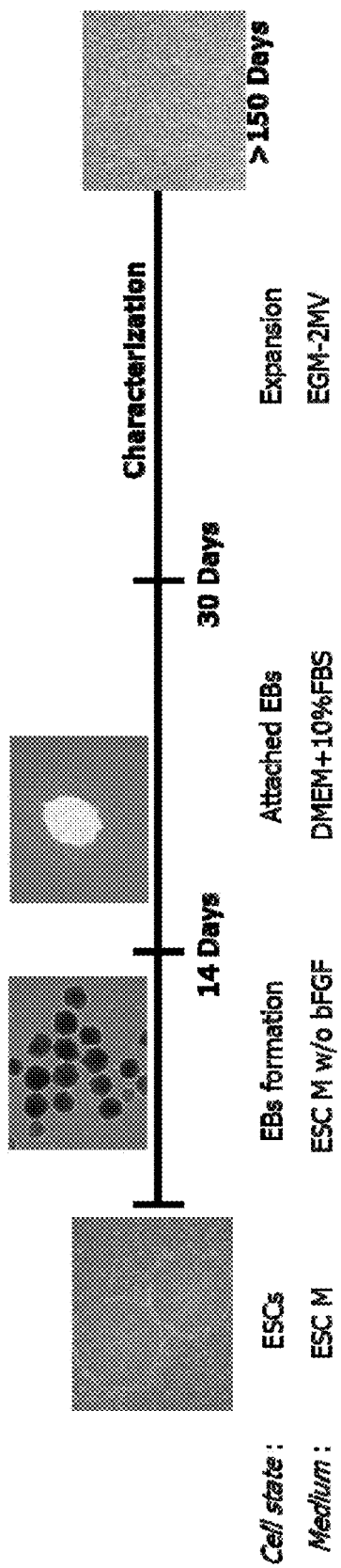
FIG. 1A shows induction of differentiation into mesenchymal stem cells from human pluripotent stem cells and proliferative culturing thereof.

The present invention is directed to a method for producing mesenchymal stem cells by using human pluripotent stem cells, the method includes: a) forming embryonic bodies from human pluripotent stem cells; b) attaching the embryonic bodies to a tissue culture dish and then inducing spontaneous differentiation of the embryonic bodies into mesenchymal stem cells; and c) maintaining and proliferatively culturing the differentiation-induced mesenchymal stem cells. Specifically, the present invention may include the formation of the embryonic bodies from the human pluripotent stem cells, and this may be carried out by a general method known in the art. For example, the human pluripotent stem cells may be treated with protease, and then cultured in a suspension state in an embryonic stem cell medium free from basic fibroblast growth factor (bFGF).

The term "stem cells" as used herein refers to master cells which can unlimitedly regenerate cells so as to form specialized cells of tissues and organs. The stem cells are developable multipotent or pluripotent cell. The stem cell may be cell-divided into two daughter stem cells, or one daughter stem cell and one transit cell, and they subsequently, proliferate to mature and complete type of cells of tissue. These stem cells may be classified by various methods. One of the most commonly used methods depends on differentiation capability of the stem cells. According to the method, the stem cells may be classified into pluripotent stem cells that are differentiable into three-germ layer cells, multipotent stem cells that are limitedly differentiable into a specific germ layer or more, and unipotent stem cells that are differentiable only into a specific germ layer.

The term "pluripotent stem cells" as used herein refers to stem cells having pluripotency, which are capable of differentiating into all three germ layers constituting a living body, and examples thereof include embryonic stem cells and induced pluripotent stem (iPS) cells. The adult stem cells may be multipotent or unipotent stem cells.

The term "differentiation" as used herein refers to a process by which cells become specialized in structure or function during division, proliferation and growth of cells, that is, change of morphology or function of cells so that cells, tissues, etc. of an organism perform given works thereof. Generally, it is a process that a relatively simple system being separated into two or more qualitatively different partial systems. The differentiation refers to a state in which parts of a certain bio-system, that have been homogeneous at first, become qualitatively distinguished from one another, or as the result thereof, they become divided into qualitatively distinguishable parts or partial systems, such as, for example, in terms of ontogenesis an egg, which was homogeneous at first, become distinguished into head, body, etc. or cells as myocytes, neurocytes, etc. become distinguished from one another.

The term "embryonic body (EB)" as used herein refers to an aggregate formed by inducing differentiation of the pluripotent stem cells. The embryonic body may be generated when the pluripotent stem cells are cultured in a suspension state without feeders in an embryonic stem cell medium free from a basic fibroblast growth factor (bFGF). The embryonic body prepared by the above method has been reported to be able to differentiate into all cells necessary for formation of an individual from endoderm, mesoderm, and ectoderm, and this corresponds to one of the in vitro methods that prove pluripotency of the pluripotent stem cells.

Figure 1B:
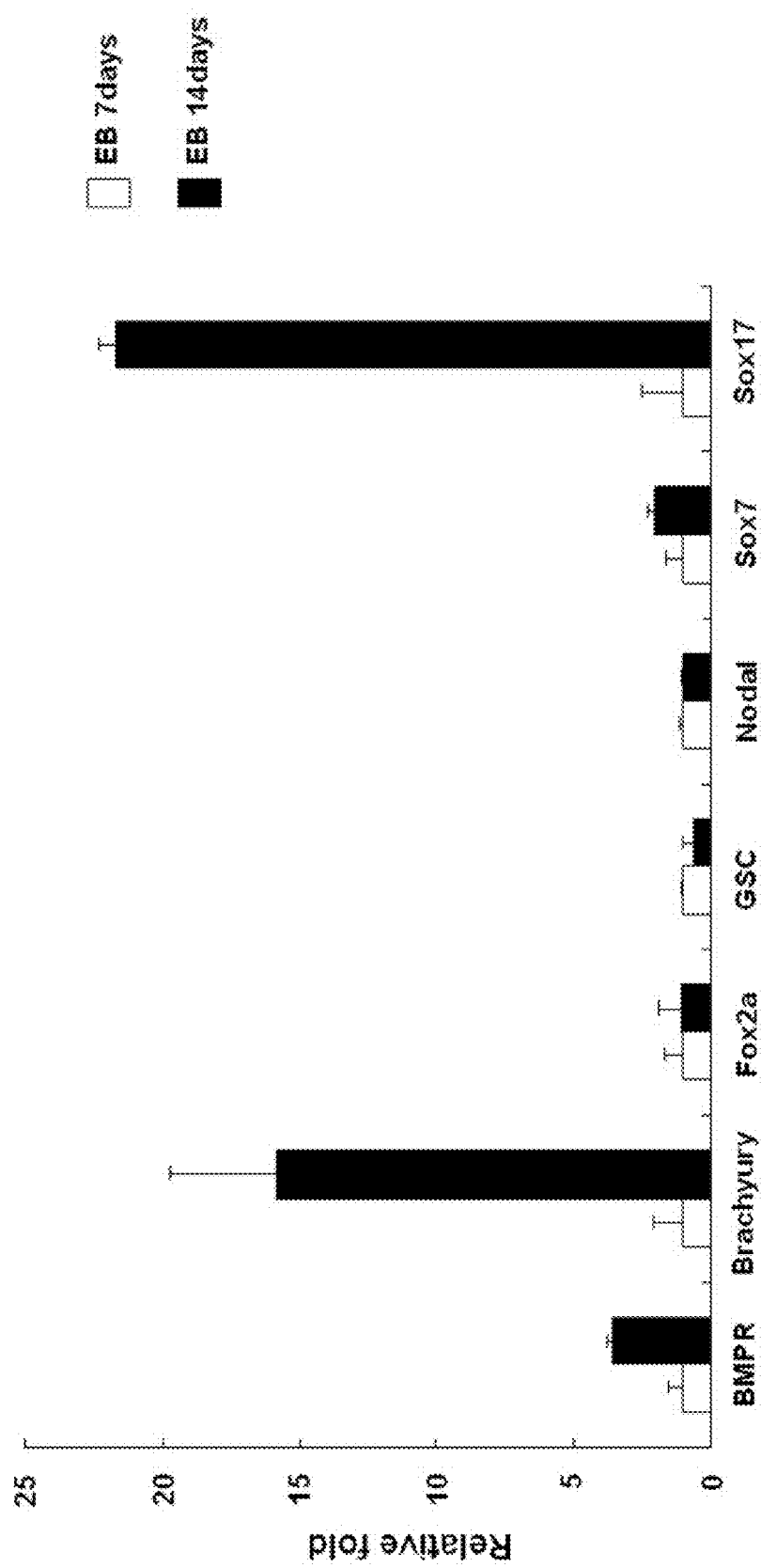
FIG. 1B shows quantification results of a difference in gene expression associated with mesenchymal differentiation of 7-day embryonic bodies and 14-day embryonic bodies by using polymerase chain reaction.

The present invention may include selecting embryonic bodies on day 14 of culture, and inducing differentiation of the embryonic bodies into the mesenchymal stem cells. Specifically, the embryonic bodies on day 14 of culture, which are formed by culturing the human pluripotent stem cells in a suspension state in an embryonic stem cell medium free from bFGF, may be selected, and then used in the production of the mesenchymal stem cells. The embryonic bodies on day 7 of culture were generally used in the existing methods for inducing differentiation into the mesenchymal stem cells from the human pluripotent stem cells (generally human embryonic stem cells). However, the present inventors found that the selection of the embryonic bodies on day 14 of culture instead of the embryonic bodies on day 7 of culture can increase differentiation-inducing efficiency in view of the production of the mesenchymal stem cells from the human pluripotent stem cells. Specifically, as the results of studying gene expression of the embryonic bodies on day 7 and on day 14 of culture, it was confirmed that genes associated with early mesenchymal differentiation (brachyury, BMPR, etc.) and Sox 17, which is an important gene in early cardiac mesenchymal cells, are remarkably highly expressed in the embryonic bodes on day 14 of culture, as compared to the existing embryonic bodies on day 7 of culture (see, FIG. 1B). It is seen from the above results that selection of the embryonic bodies on day 14 of culture can induce preferential differentiation into the mesenchymal stem cells.

Figure 2A:
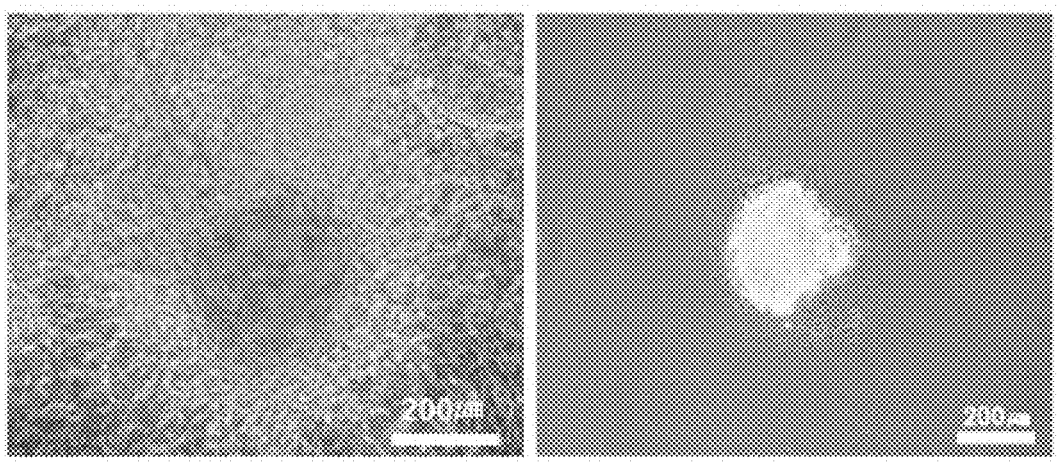
FIG. 2A shows sorting of embryonic bodies on day 14 at the time of attachment thereof.

In addition, the present invention may include attaching the embryonic bodies on day 14 of culture to a tissue culture dish, and then inducing spontaneous differentiation of the embryonic bodies into mesenchymal stem cells. When inducing differentiation into the mesenchymal stem cells from the human pluripotent stem cells is induced, it is normal to initiate the induction of differentiation by external addition of bone morphogenic protein (BMP)-2 etc. The present inventors found that spontaneous differentiation into the mesenchymal stem cells was induced when the embryonic bodies were cultured by using a general cell culture medium such as Dulbecco's Modified Eagle's Medium (DMEM) medium, etc. without external addition of BMP-2 etc. (see, FIG. 2B). In relation to this mechanism, the present inventors considered the possibility of auto-loop formation of BMP, which is a mesenchymal stem cell inducing factor, known to the related art, and then, in order to prove this, observed an induction process of differentiation of the mesenchymal stem cells through treatment with Noggin which is a BMP antagonist (see, FIGS. 2C and 2D). The differentiation into the mesenchymal stem cells was induced in a Noggin-untreated group (see, FIG. 2C). However, it was observed that the mesenchymal progenitor cells do not appear in a Noggin-treated group (see, FIG. 2D), and also, at the time of passaged culture, cell culturing was impossible since the cells could not be re-attached. It can be seen from the above results that, when the embryonic bodies on day 14 of culture are cultured in a general culture medium after attachment thereof, spontaneous differentiation into the mesenchymal stem cells is induced even without external addition of cytokine, and this is due to self regulation by a BMP loop system.

In addition, the present invention may include maintaining and proliferatively culturing the differentiation-induced mesenchymal stem cells by using a medium containing cytokine. In the present invention, a microvascular endothelial cell media-2 (EGM-2MV, Lonza; Basel, Switzerland) medium containing human epidermal growth factor (hEGF), vascular endothelial growth factor (VEGF), human fibroblast growth factor-basic (hFGF-B), insulin-like growth factor (IGF-1), hydrocortisone, and ascorbic acid, etc. was used as a culture medium of the mesenchymal stem cells. The present inventors found that activity of the mesenchymal stem cells was maintained relatively longer in their in vitro culture, when the EGM-2MV medium was used instead of the α-MEM medium which has been widely used as the existing mesenchymal stem cell culturing medium.

In order to use the mesenchymal stem cells as cell therapy products, supplying a sufficient amount of cells as described above must be put first, and for that purpose, passaged culture of the mesenchymal stem cells is needed. However, repeated passaged culture may cause senescence of the mesenchymal stem cells, resulting in deterioration of division capability thereof, and thus, activity (differentiation capability) thereof may be lost. In this regard, it was confirmed that the EGM-2MV medium of the present invention had superior activity-retaining capability, compared to the α-MEM medium that has been used as the existing mesenchymal stem cell culturing medium. (see, FIG. 3). Specifically, as the result of carrying out beta gal staining by which cells are stained at the time of senescence thereof, it has been seen that the beta-gal staining of more cells was done and size of the cells became remarkably larger in the mesenchymal stem cells cultured by using the α-MEM medium than in the mesenchymal stem cells cultured by using the EGM-2MV medium. It has been generally known that, at the time of in vitro culture of stem cells, non-growth thereof due to cell senescence is associated with enlargement of cells. This means that, when the mesenchymal stem cells are cultured by using the α-MEM medium, the senescence of the mesenchymal stem cells is accelerated, and thus, differentiation capability of the mesenchymal stem cells is lost.

In addition, the present invention provides mesenchymal stem cells produced by the method of the present invention. The mesenchymal stem cells can differentiate into osteocytes, chondrocytes, and myocytes, etc., and defined by a spiral form, and degree of expression of basic cell surface markers, SH2(+), SH3(+), CD34(−), and CD45(−). Mesenchymal stem cells derived from human embryonic stem cells of Seoul National University Hospital (Asian #1, male, STO feeder) obtained through the method of the present invention derived the same results under three different trials, which were confirmed by a fluorescent activated cell sorter and through functional differentiation.

The present invention provides a standardized method for inducing of differentiation and proliferative culturing, which can be used generally to produce mesenchymal stem cells from human pluripotent stem cells having various genetic origins. In this regard, the method of the present invention was performed on human embryonic stem cells of Cha Medical Center (Asian #2, male, MEF feeder) and H9 human embryonic stem cells (Westerner, female, MEF feeder), which have different genetic origins from the human embryonic stem cells of Seoul National University Hospital, and the same results were obtained therefrom. That is to say, the standardized method of the present invention can be used generally in order to induce differentiation of the mesenchymal stem cells from human pluripotent stem cells having various genetic backgrounds and/or culture environments.

In addition, the present invention provides cell therapy products including the mesenchymal stem cells obtained by the method of the present invention. Specifically, the cell therapy products can be used for the formation of adipocytes, osteocytes, chondrocytes, myocytes, neurocytes and cardiomyocytes and the differentiation into various cells according to the environments.

The term "cell therapy product" as used herein refers to a drug for the purpose of treatment, diagnosis, and prevention comprising cells or tissues prepared from humans by isolation, culture and specialized manipulations (U.S. FDA guidance), more particularly, to a drug for the purpose of treatment, diagnosis, and prevention, prepared by any process including proliferating or sorting autologous, homologous or heterologous live cells in vitro, or modifying the biological characteristics of cells by other methods, so as to restore the function of cells or tissues. The cell therapy products are largely classified into somatic cell therapy products and stem cell therapy products according to the degree of cell differentiation, and the present invention is specifically directed to a stem cell therapy product.

In addition, the present invention provides a system for producing mesenchymal stem cells from human pluripotent stem cells having various genetic origins. The system includes: a) culturing human pluripotent stem cells and selecting embryonic bodies on day 14 of the culture; b) attaching the embryonic bodies to a tissue culture dish and culturing the embryonic bodies by using DMEM+FBS medium inducing, thereby to induce differentiation of the embryonic bodies; c) and maintaining and proliferatively culturing the mesenchymal stem cells by using a medium containing human epidermal growth factor (hEGF), vascular endothelial growth factor (VEGF), human fibroblast growth factor-basic (hFGF-B), insulin-like growth factor (IGF-1 hydrocortisone, and ascorbic acid.

Figure 10:
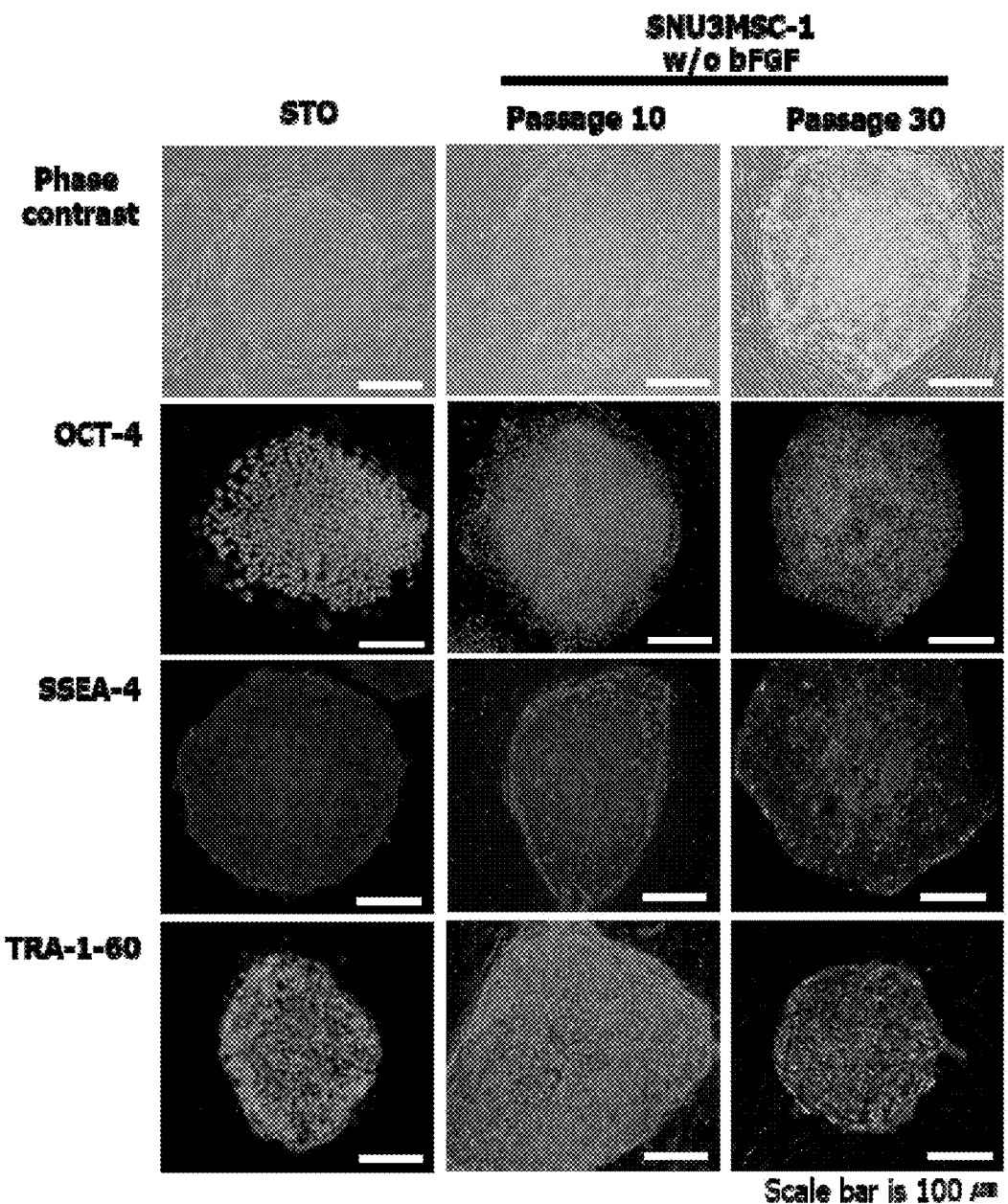
FIG. 10 shows experimental results on the possibility of the mesenchymal stem cells obtained by the method of the present invention as autologous feeders.

In addition, the present invention provides a feeder for a culturing human pluripotent stem cells. The feeder is needed in order to continuously maintain an undifferentiated state of the human pluripotent stem cells in the culture thereof. Fibroblast derived from mouse embryo has been preferentially used as the existing feeders for the human pluripotent stem cells. However, since interspecies infiltration of various pathogens has been recognized as a problem when the pluripotent stem cells are to be used clinically, several cells derived from human have been reported to be possible as feeders as an alternative. However, this also could not overcome disadvantages: absolute exclusion of heterologous pathogens was impossible; foreign factors to maintain undifferentiated state (for example, bFGF, IGF, and ACTIVIN, etc.) are needed essentially; and continuous supply of cells for long culture is impossible. On the contrary, the mesenchymal stem cells derived from the human pluripotent stem cells, which are produced according to the present invention, can continuously supply cells having the identical background, and also can exclude immunological rejection and/or infiltration of other pathogens as autologus feeders. Furthermore, the present inventors found merit that foreign undifferentiated state-maintaining factors are not needed when the mesenchymal stem cells derived from the human pluripotent stem cells, which are produced according to the present invention, are used as feeders. In other words, it was confirmed that the undifferentiated state was maintained even without the addition of undifferentiated state-maintaining factors for 30 or more passages (see, FIG. 10), and this remarkable effect, "maintaining an undifferentiated state for a long time" could not be obtained even when the existing several feeders derived from a human are used under the addition of an excessive quantity of factors for maintaining the undifferentiated state.

Hereinafter, the present invention will be described in detail with reference to examples below. However, the following examples are for merely exemplifying the present invention, and therefore, the scope of the present invention is not limited to the following examples. It is obvious that various modifications made by those skilled in the art are all included within the technical scope of the present invention.

EXAMPLES

Example 1

Production of Mesenchymal Stem Cells from Human Embryonic Stem Cells of Seoul National University Hospital (1) Formation of Embryonic Bodies Human embryonic stem cells of Seoul National University Hospital (Asian #1, male, STO feeder), which were maintained in an undifferentiated state, were treated with dispase (2 mg/ml), followed by isolation through fine working, and then cultured in a suspension state in an embryonic stem cell medium free from bFGF for 14 days.

Figure 1C:
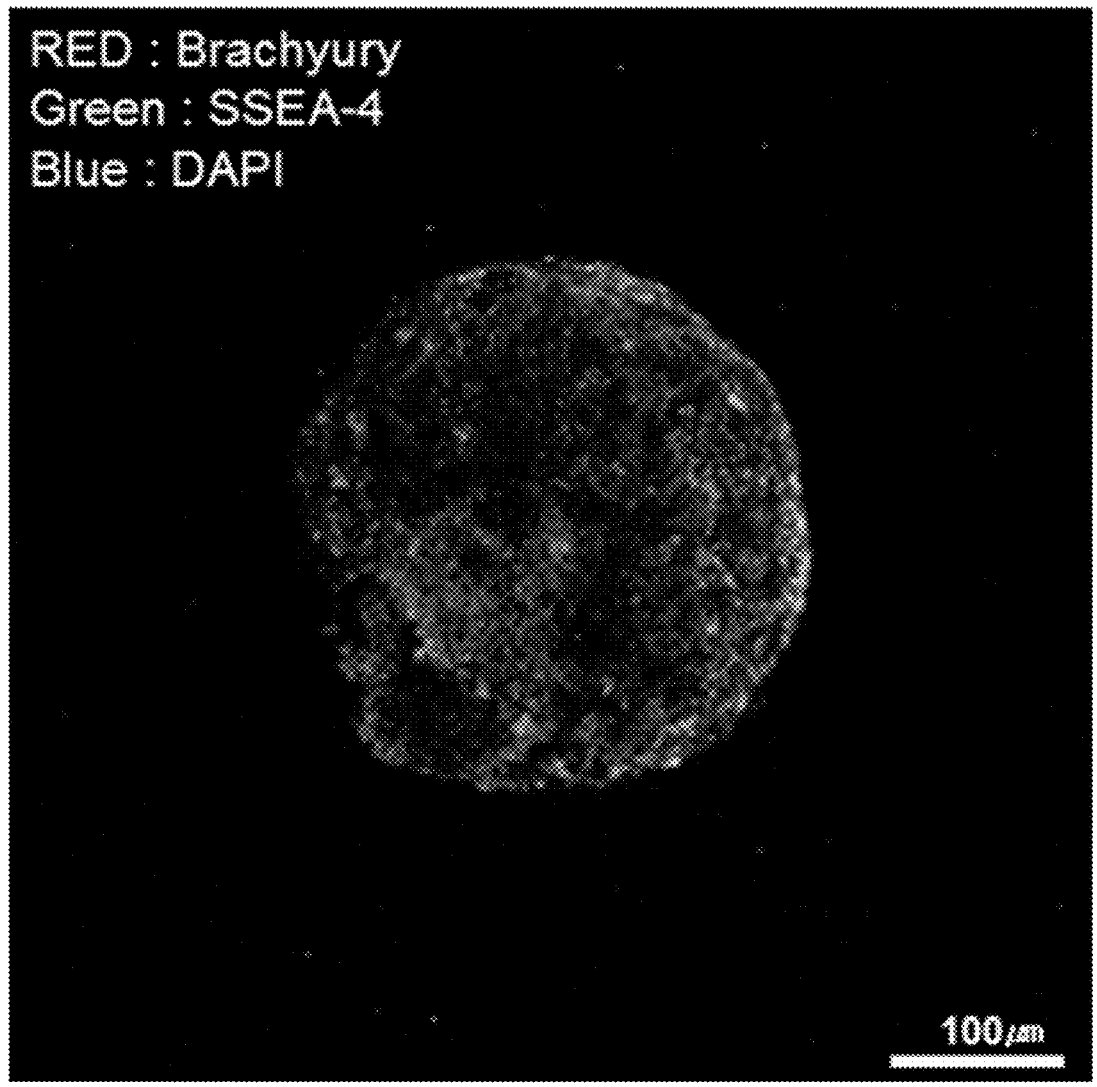
FIG. 1C shows confirmation results of protein expression of genes at the early stage of mesenchymal differentiation by staining 14-day embryonic bodies.

Gene analysis was performed on the embryonic bodies on day 7 and on day 14 of culture, and a difference in gene expression associated with mesenchymal differentiation for respective embryonic bodies was quantified by using polymerase chain reaction (PCR). It was confirmed that brachyury and BMPR, which are genes associated with early mesenchymal differentiation, and Sox 17, which is an important gene in early cardiac mesenchymal cells, are remarkably highly expressed in the embryonic bodies on day 14 of culture, compared to the embryonic bodies on day 7 of culture (see, FIG. 1B). In addition, protein expression of brachyury and location thereof were confirmed through staining of the embryonic bodies on day 14 of culture (see, FIG. 1C).

(2) Induction of Differentiation into Mesenchymal Stem Cells

The embryonic bodies prepared by suspension culture for 14 days were attached to a tissue culture dish, and then induced natural differentiation into mesenchymal stem cells. The sorting of the embryonic bodies on day 14 at the time of attachment was shown in FIG. 2A. After the attachment, some embryonic bodies were well growing (a left image of FIG. 2A), and other embryonic bodies were not well growing (a right image of FIG. 2A). Induction of differentiation into mesenchymal stem cells was observed, while the embryonic bodies were cultured in a medium comprising Dulbecco's Modified Eagle's Medium (DMEM) and fetal bovine serum (10% v/v) for 16 days. The observation results on the $3^{rd}$ day and the $7^{th}$ day after attachment of the embryonic bodies were shown in FIG. 2B.

Figure 2B:
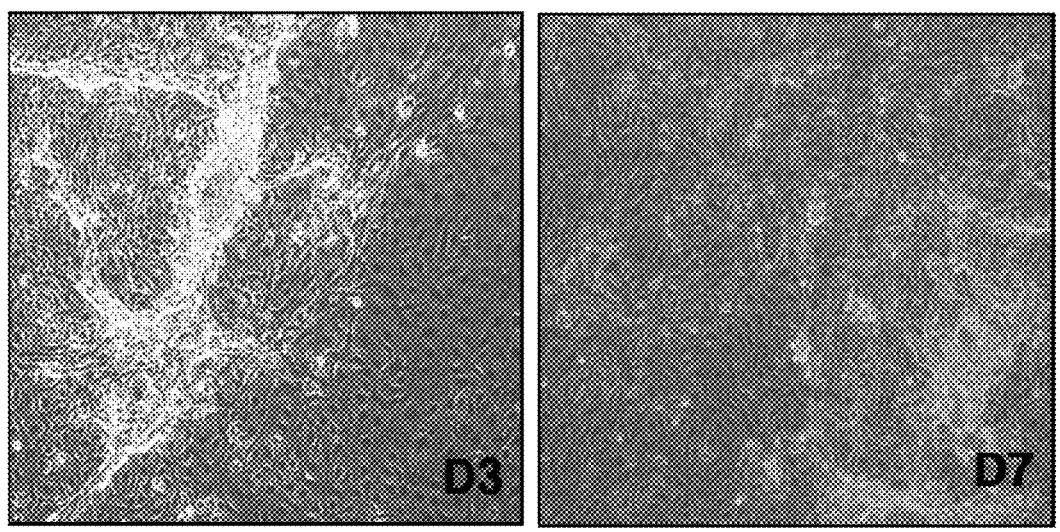
FIG. 2B shows that induction of differentiation into mesenchymal stem cells is initiated when the embryonic bodies are cultured in a general culture medium, which do not add external cytokine. This figure shows the culture three days (left panel) and seven days (right panel) after attachment of the embryonic bodies.
Figure 2C:
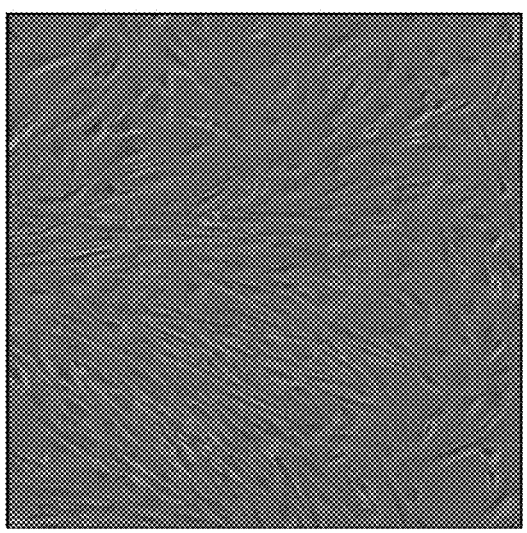
FIGS. 2C and 2D show induction process of differentiation into mesenchymal stem cells in a group untreated with and treated with Noggin which is BMP antagonist, respectively.
Figure 2D:
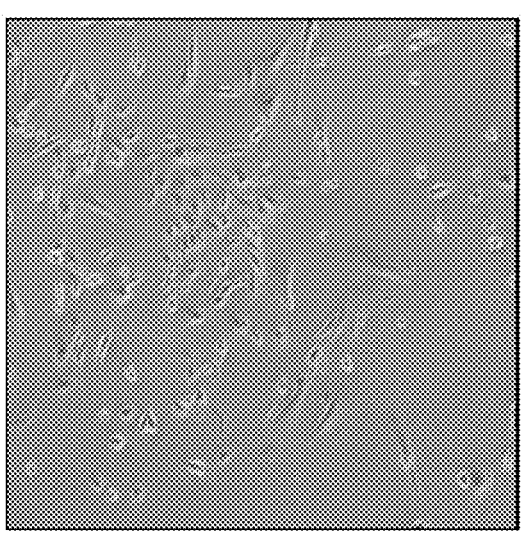

As seen from FIG. 2B, it was confirmed that the induction of spontaneous differentiation of the embryonic bodies into mesenchymal stem cells was initiated when the embryonic bodies were cultured in a general culture medium (DMEM+FBS) without cytokine. In order to uncover the mechanism of the induction of differentiation, process of induction of differentiation into the mesenchymal stem cells through treatment with Noggin, which is BMP antagonist were compared and observed (see, FIGS. 2C and 2D). It was confirmed that the differentiation into the mesenchymal stem cells was induced in a Noggin-untreated group (see, FIG. 2C), whereas the mesenchymal progenitor cells were not observed in a Noggin-treated group (see, FIG. 2D). It can be seen from the above results that, when the embryonic bodies are cultured in a general culture medium without external addition of cytokine, the induction of spontaneous differentiation into the mesenchymal stem cells is due to by a BMP auto feedback loop system.

(3) Maintaining and Proliferative Culturing of Differentiation-Induced Mesenchymal Stem Cells The mesenchymal stem cells, which are differentiation-induced by culturing the embryonic bodies for 16 days after attachment thereof in (2) of Example 1, were treated with enzymes (Trypsin-EDTA, 0.25% Trypsin with EDTA 4Na), and were segregated into single cells, which were then again attached to a tissue culture dish. Then, the cells were maintained and proliferatively cultured at 37° C., by using 500 Mg of culture medium comprising, 0.5 mg of human epidermal growth factor (hEGF), 0.5 mg of vascular endothelial growth factor (VEGF), 2 mg of human fibroblast growth factor-basic (hFGF-B), 0.5 mg of insulin-like growth factor (IGF-1), 0.2 mg of hydrocortisone, and 0.5 ml of ascorbic acid, plus 470 ml of a basic medium.

Regarding whether or not activity of the mesenchymal stem cells was maintained during the proliferative culture, activity-maintaining capabilities in the EGM-2MV medium used in the present invention and the α-MEM medium, which is the existing mesenchymal stem cell culture medium, were compared with each other through an experiment. Specifically, senescence-associated beta-gal staining was performed on the cell groups cultured by using the respective media, and the results were shown in FIG. 3 (culturing and comparison were carried out for a month, and the cells of $7^{th}$ culture passage were used).

Figure 3:
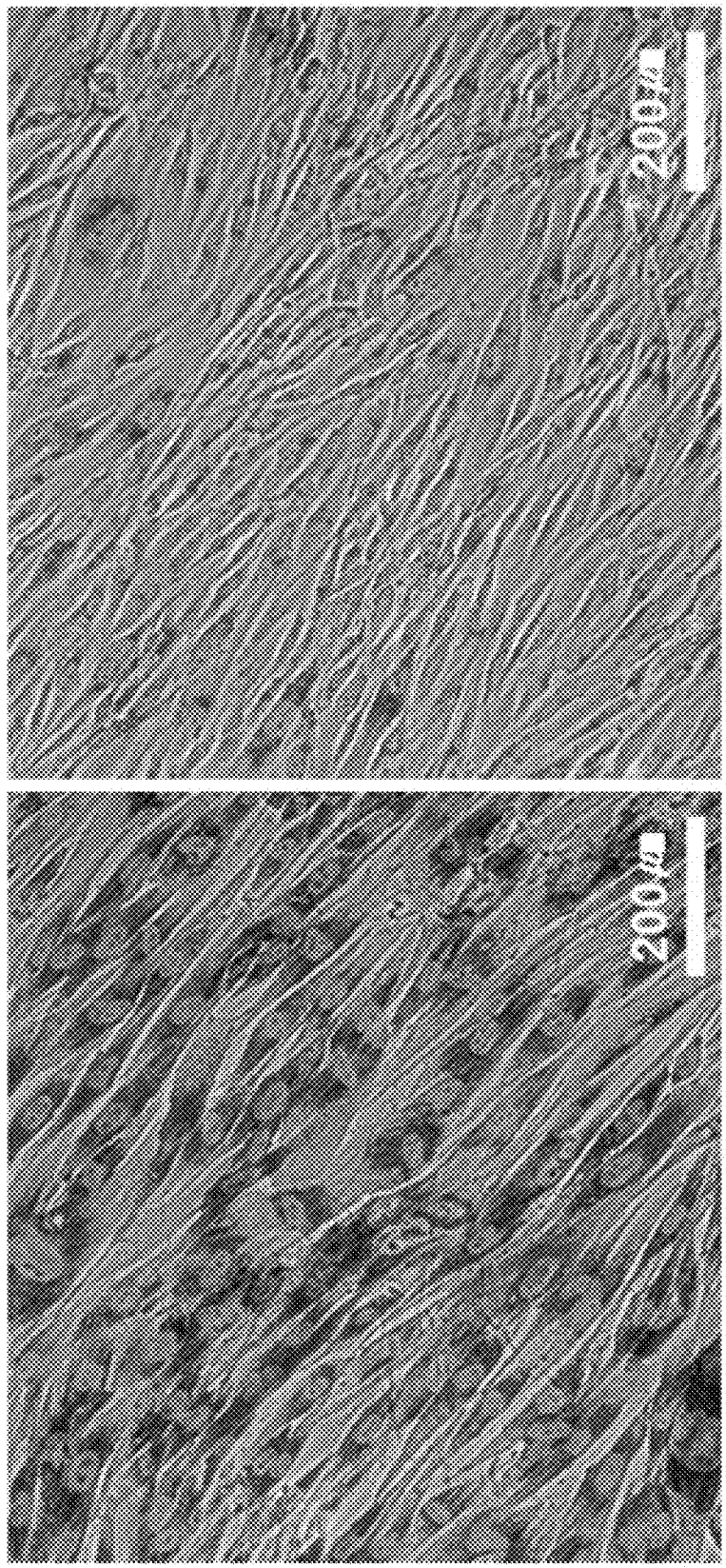
FIG. 3 shows a difference in efficiency between an EGM-2MV medium and an A-MEM medium, which is the existing medium for culturing mesenchymal stem cells, that confirmed by beta-gal staining associated with cell senescence.

It is shown in FIG. 3 that beta-gal staining of more cells was done in the mesenchymal stem cells cultured by using the α-MEM medium than in the mesenchymal stem cells cultured by using the EGM-2MV medium. This means that, when the mesenchymal stem cells are cultured by using the α-MEM medium, the senescence of the mesenchymal stem cells is accelerated, and thus, differentiation capability of the mesenchymal stem cells is lost, and finally, the mesenchymal stem cells cannot serve as cell therapy products. Whereas, the use of the EGM-2MV medium of the present invention can maintain activity of the mesenchymal stem cells for a long time in spite of successive passaged culture, and thus, can relatively improve practicability as the cell therapy products, compared to the use of the α-MEM medium.

Figure 4A:
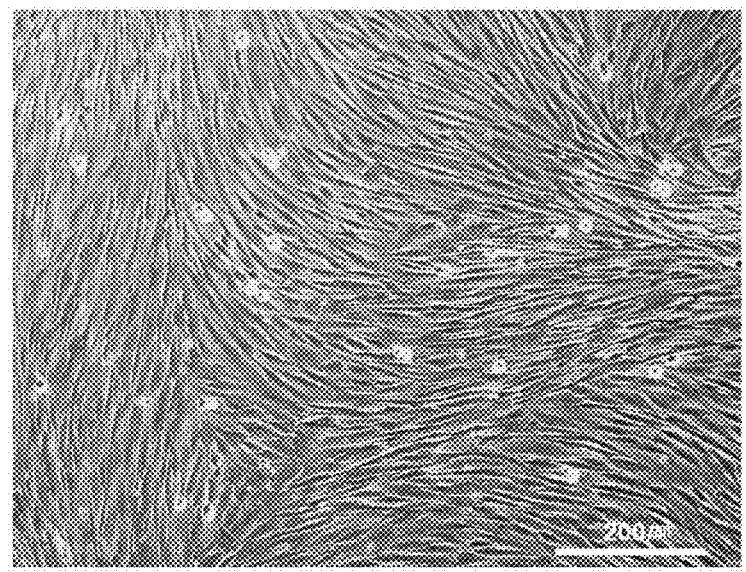
FIG. 4A shows a growth pattern of mesenchymal stem cells cultured in the EGM-2MV medium for 140 days or longer.
Figure 4B:
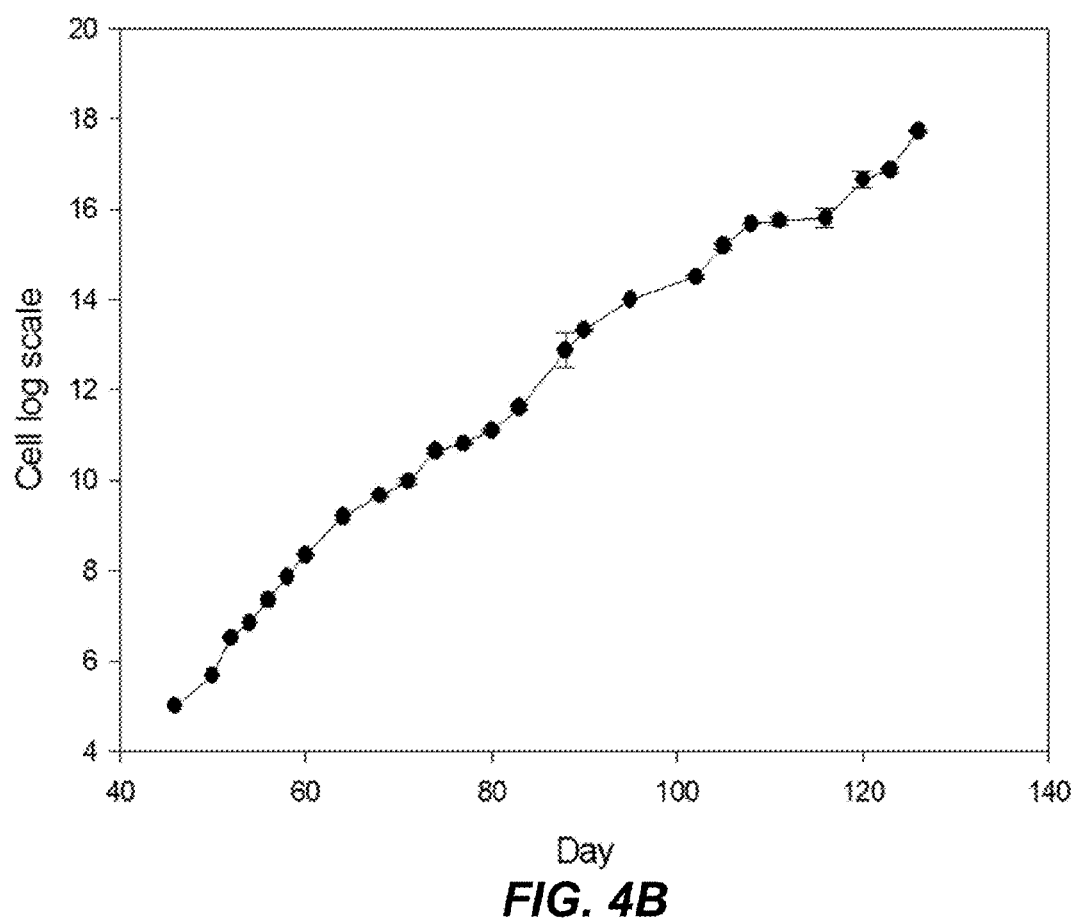
FIG. 4B is a growth curve of mesenchymal stem cells of the present invention showing that they grow while maintaining long term activity when cultured in vitro.

In addition, it is examined whether or not identity and activity of the mesenchymal stem cells can be continuously maintained when the mesenchymal stem cells are cultured for a long time by using the EGM-2MV medium, and the results thereof were shown in FIG. 4. FIG. 4A shows cells after 140-day or more culture by using the EGM-2MV medium, and it shows that the growth shape of the cells still has a finger printing pattern, which is a typical pattern of the mesenchymal stem cells. FIG. 4B shows that cell division continuously and vigorously occurs until 140 days of culture, and it is shown that activity of the mesenchymal stem cells can be continuously maintained. In conclusion, it can be clearly seen that identity and activity of the mesenchymal stem cells can be maintained for a long time when the differentiation-induced mesenchymal stem cells are maintained and proliferatively cultured in the EGM-2MV medium of the present invention.

Example 2

Characterization of Mesenchymal Stem Cells (1) Analysis of Cell Surface Markers

It was analyzed whether or not cell surface markers specific to the mesenchymal stem cells obtained in Example 1 are expressed. The results which are obtained by using a fluorescent activated cell sorter after the antigen-antibody reaction were shown in FIG. 5. IgG, was used as a control.

Figure 5A:
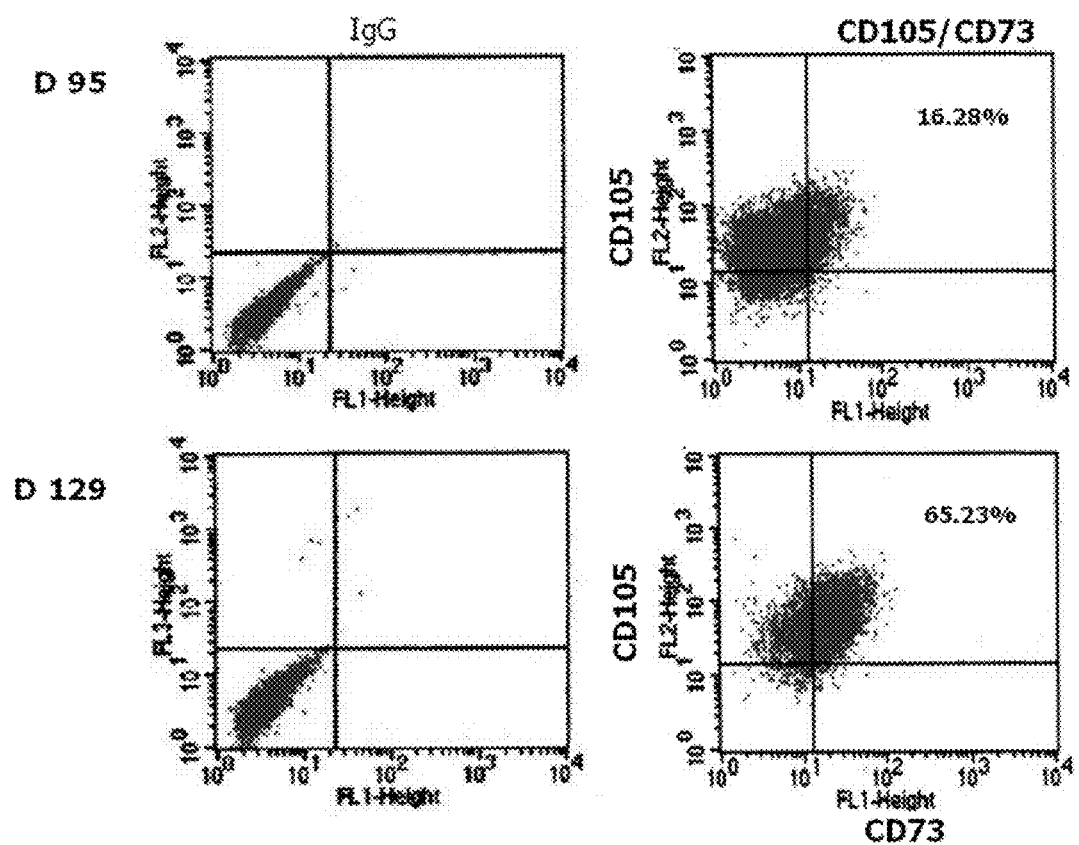
FIGS. 5A and 5B show that the mesenchymal stem cells obtained by the method of the present invention express mesenchymal-specific markers.
Figure 5B:
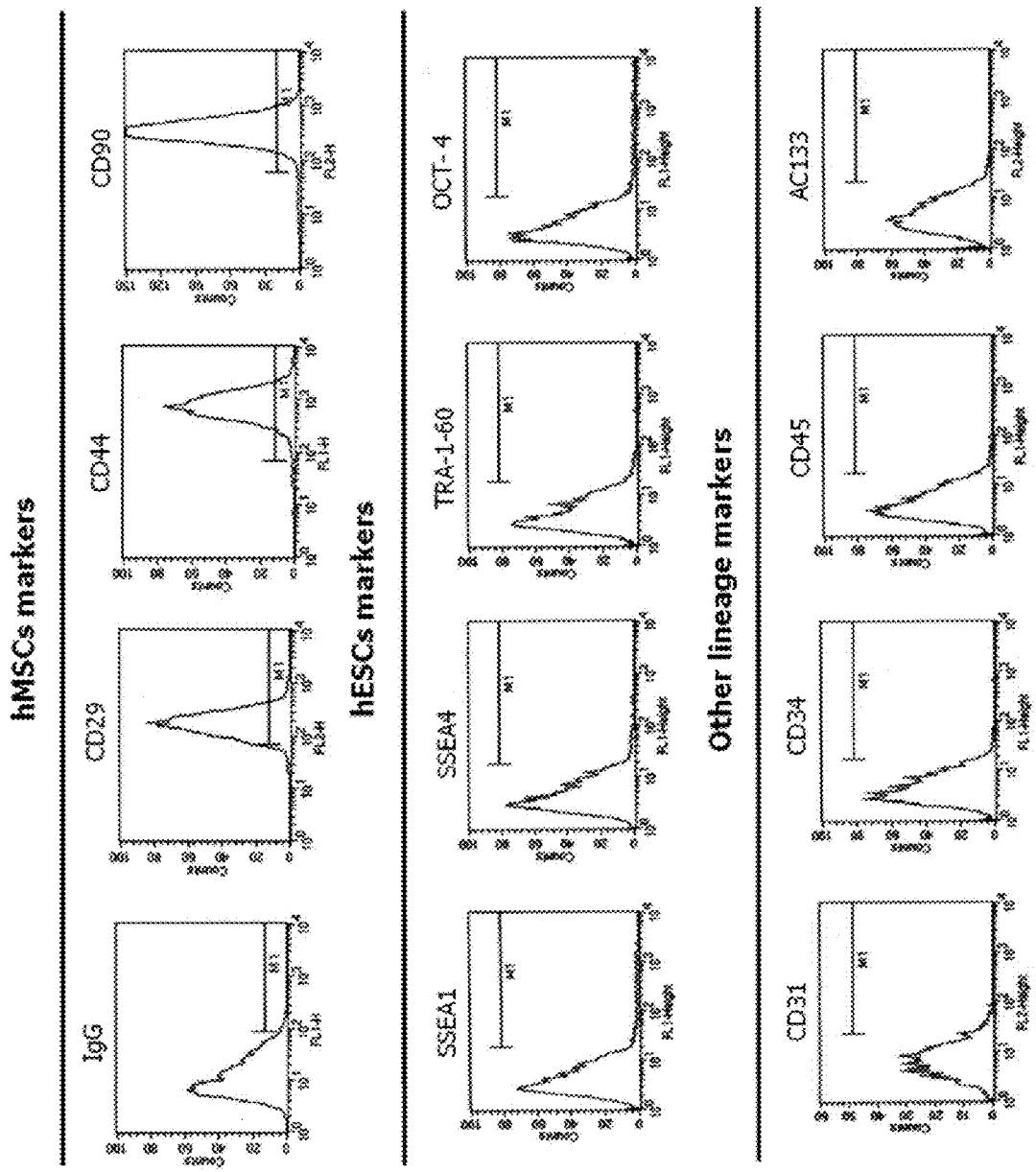

It was confirmed from FIG. 5A, that CD73 and CD105, which are markers specific to the mesenchymal stem cells, were expressed still in a large amount, in the cells on day 95 of culture (D95) and on day 129 of culture(D129). In addition, cell surface marker analysis was performed on the mesenchymal stem cells on day 129 of culture, and the results were shown in FIG. 5B. It was confirmed from FIG. 5B, that CD29, CD44, and CD90, which are human mesenchymal stem cell (hMSC) markers, were expressed, but neither SSEA1, SSEA4, TRA-1-60, and OCT-4, which are human embryonic stem cell (hESC) markers, nor endoderm and ectoderm markers (other lineage markers) were expressed.

Finally, according to the method of the present invention, it is clearly shown that differentiation of only the mesenchymal stem cells are selectively induced from the human pluripotent stem cells, and further, identity of the mesenchymal stem cells can be still maintained at the time of long proliferative culturing of the cells.

(2) Karyotype Analysis

Figure 6:
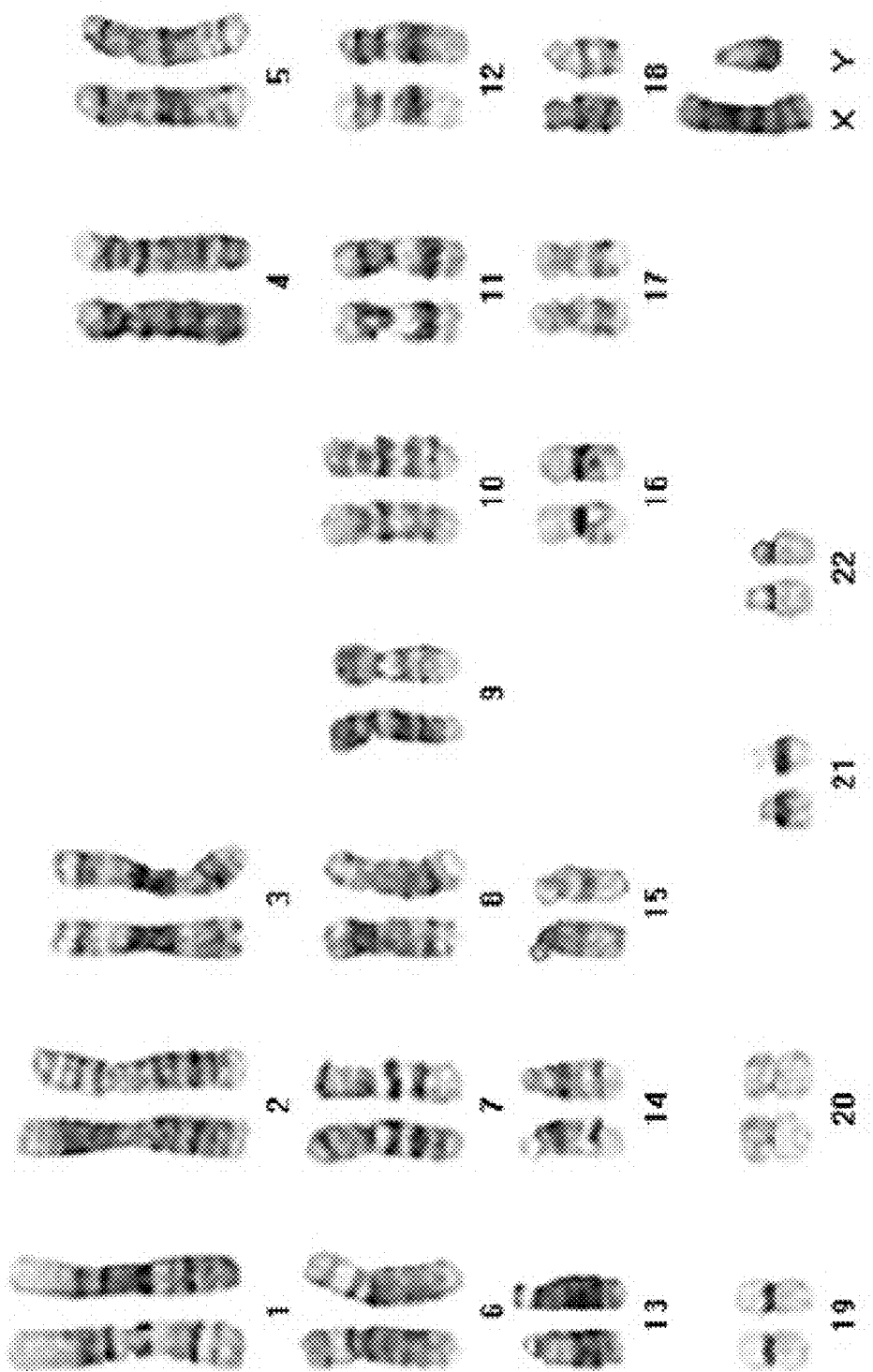
FIG. 6 shows chromosome analysis results of the mesenchymal stem cell of the present invention after long-term in vitro culture thereof.

The karyotype of the mesenchymal stem cells (on day 160 of culture) obtained in Example 1 was analyzed by using a G-banding method (Saccone et al., Proc. Natl. Acad. Sci. USA, 89: 4913-4917, 1992), and the results were shown in FIG. 6. It was confirmed from FIG. 6, that the mesenchymal stem cell had normal karyotype of XY+44.

Figure 7A:
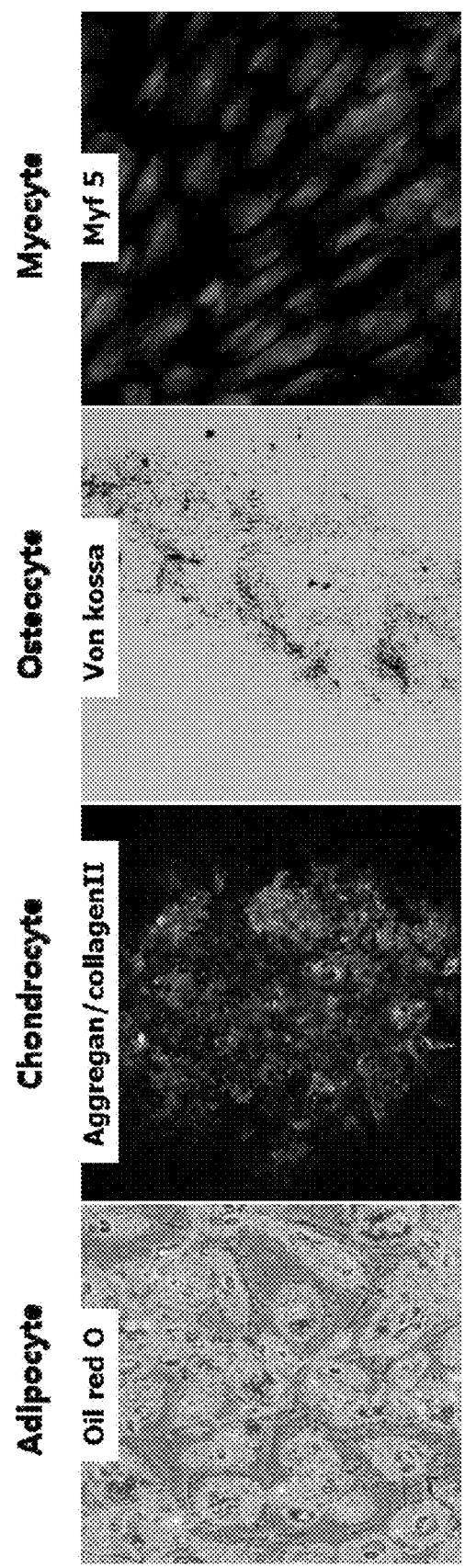
FIGS. 7A and 7B show analysis results differentiation capability of the mesenchymal stem cells obtained by the method of the present invention.

(3) Confirmation of Function (Differentiation Capability) of Mesenchymal Stem Cells In order to confirm differentiation capability of the mesenchymal stem cells (on 129 days of culture) obtained in Example 1, analysis was carried out by using the method previously reported (Tiziano Barberi et al., PLoS Medicine, 2:0554-0560, June 2005; and Kitsie J. Penick et al., Biotechniques, 39:687-691, 2005). Specifically, the differentiation into adipocytes, chondrocytes, osteocytes, and myocytes from the mesenchymal stem cells was induced, and then gene expression specific to the respective cells was examined by an immunostaining reaction. The cell differentiation results were shown in FIG. 7A.

The adipocytes were stained with Oil Red O which stains adipocyte droplets, and the chondrocytes were stained with aggrecan and collagen II, which are specific expression proteins thereto, by using an antigen-antibody reaction. Furthermore, differentiation of the osteocytes was confirmed by Von Kossa staining that can confirm formation of minerals, and differentiation of the myocytes was confirmed by MYF 5, which is a specific expression protein thereto, using an antigen-antibody reaction.

Figure 7B:
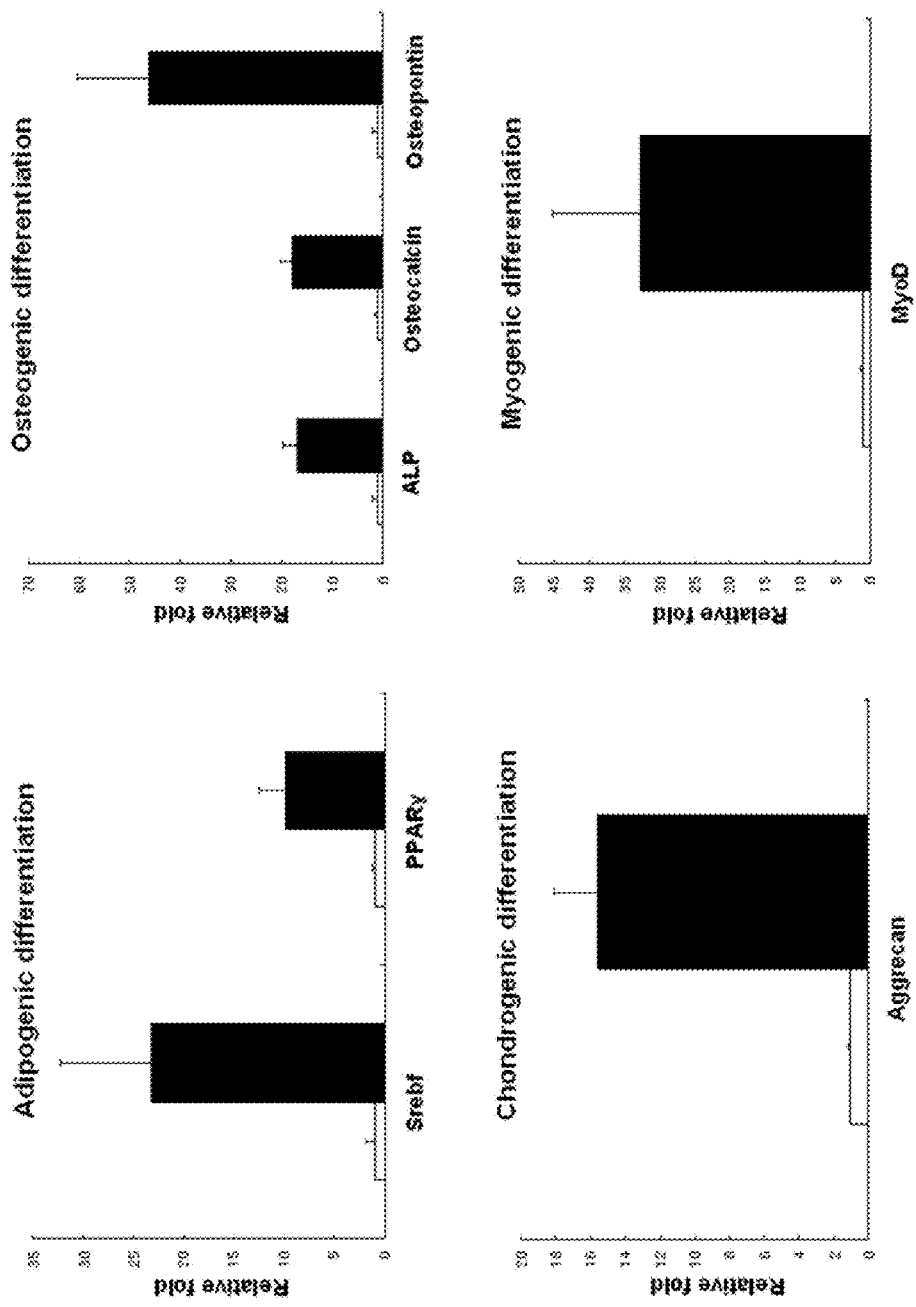

In addition, expressions of respective genes specific to the adipocytes, chondrocytes, osteocyte, and myocytes were quantified by PCR when the mesenchymal stem cells were differentiated into the respective cells, and the results were shown in FIG. 7B. It was confirmed from FIG. 7B, that Serbf and PPARγ in the adipocytes, ALP, Osteocalcin, and Osteopontin in the osteocytes, Aggrecan in chondrocytes, and MyoD in the myocytes were expressed, respectively. It is clearly shown from the above results, which the mesenchymal stem cells obtained according to the method of the present invention retain pluripotency to differentiate into the adipocytes, chondrocytes, osteocytes, and myocytes.

(4) Confirmation of Tumorigenesis Using Immuno-Deficient Mice

Figure 8A:
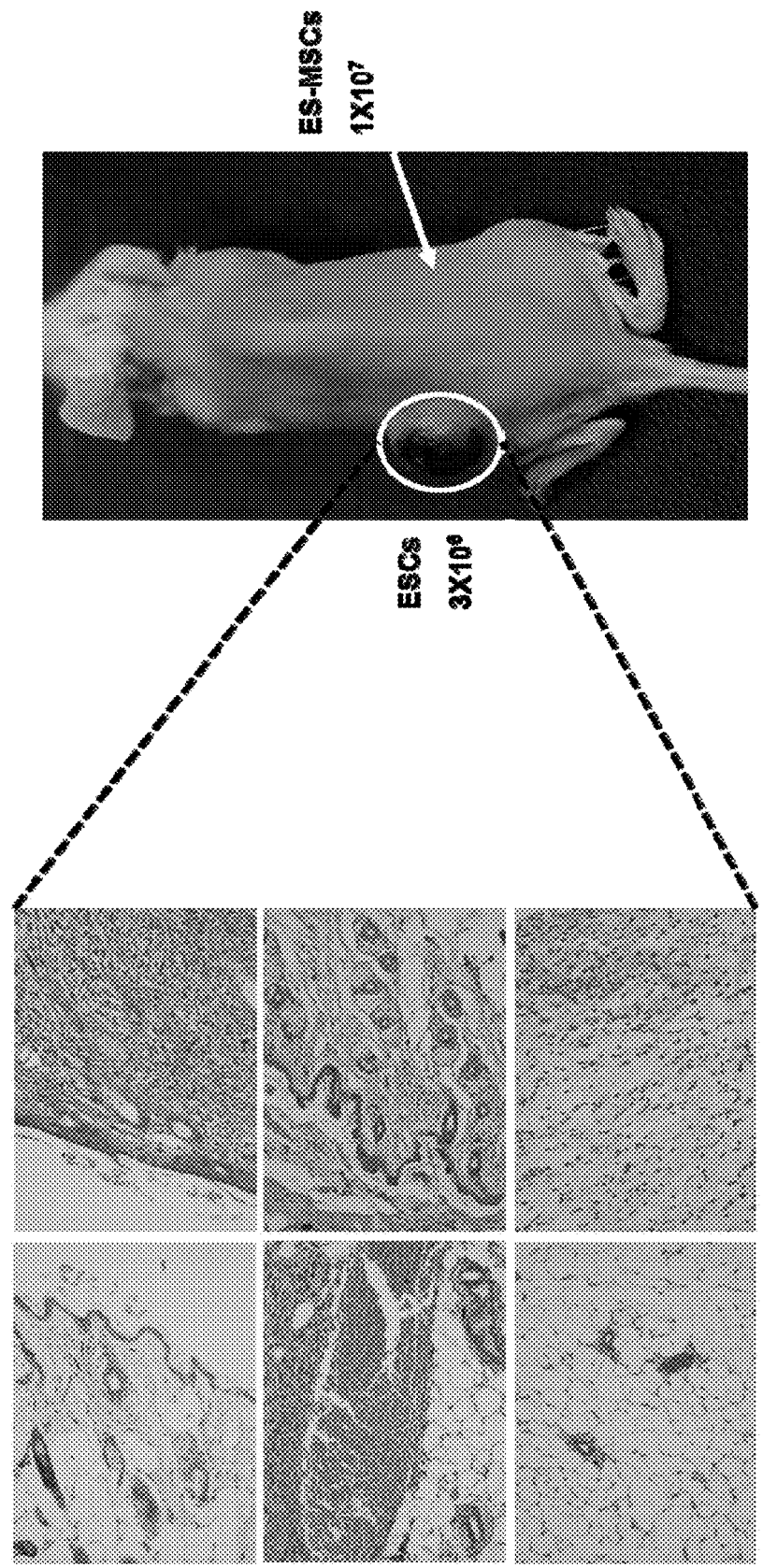
FIGS. 8A and 8B show whether or not teratoma is formed and factors associated with immune induction are expressed, by the mesenchymal stem cell obtained by the method of the present invention.
Figure 8B:
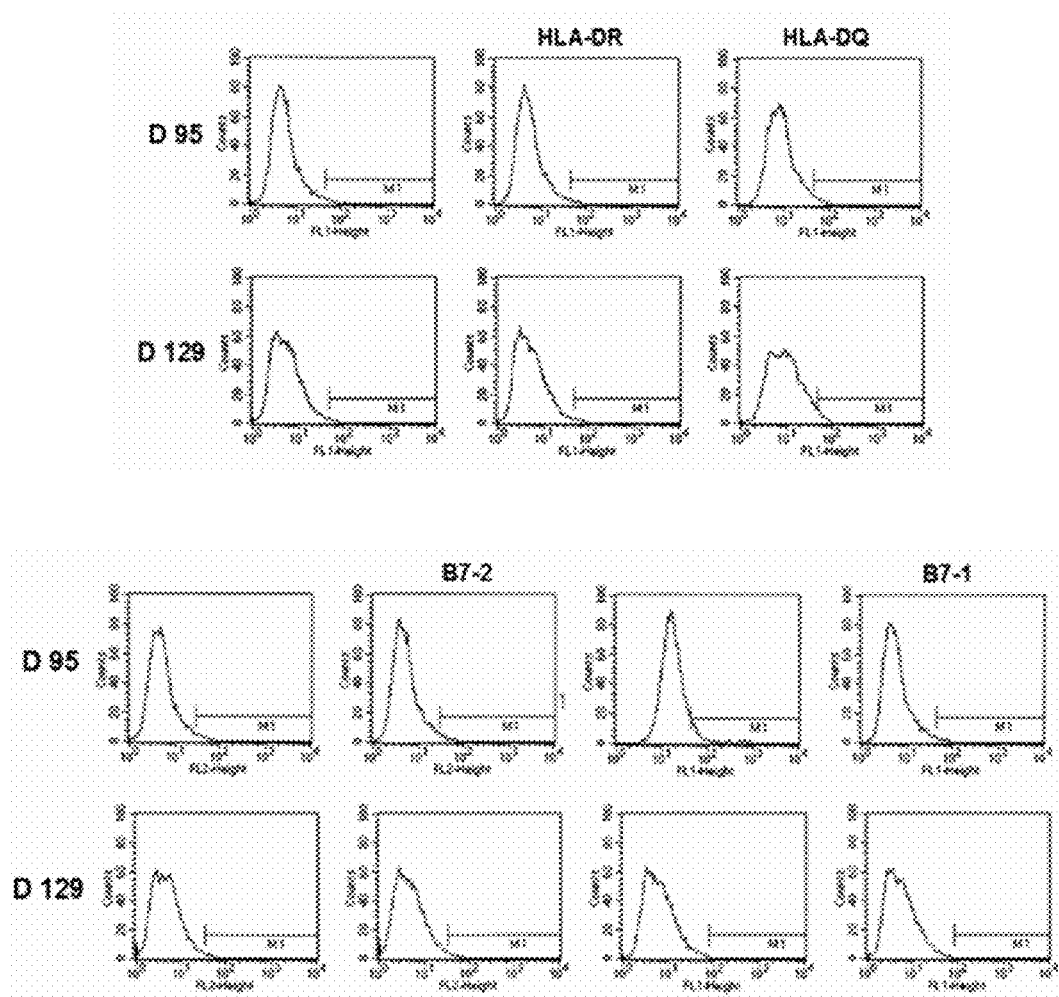

It was confirmed whether the mesenchymal stem cells of the present invention obtained by using immuno-deficient mice in Example 1 were tumorigenesis or not. Human embryonic stem cells were used for a control experiment. Specifically, $1 \times 10^7$ of the mesenchymal stem cells and $3 \times 10^6$ of human embryonic stem cells of Seoul National University Hospital were injected into the immuno-deficient mice, and the autopsy results after 12 weeks were shown in FIG. 8A. It was confirmed from FIG. 8A, that teratoma was generated in the mice into which the human embryonic stem cells of Seoul National University Hospital were injected, and the teratoma was not generated in the mice into which the mesenchymal stem cells of the present invention were injected. In addition, it was confirmed by FACS that factors associated with immune induction were not expressed, and the results were shown in FIG. 8B. IgG, was used as a control. It was confirmed from FIG. 8B, that HLA-DR and HLA-DQ, which are MHC II molecules expressed due to presence of immunogenicity, were not expressed as surface factors, and B7-2 and B7-1, which are co-simulators associated with immune induction, were not expressed.

In conclusion, it was confirmed that tumor were not induced even when the mesenchymal stem cells of the present invention were transplanted into the mice in an amount of about three or more times the number of embryonic stem cells, the control, and factors associated with immune induction were not expressed even during a long culture of 12 weeks. Therefore, it is clearly shown that the mesenchymal stem cells of the present invention are free from the risk of tumorigenesis.

(5) Functionality Assessment Using an Ischemic Cardiovascular Disease Model

In order to estimate functionality of the mesenchymal stem cells of the present invention obtained from Example 1 with respect to ischemic cardiovascular disease, an ischemic cardiovascular disease mouse model was used. After $5 \times 10^4$ of the mesenchymal stem cells (on 129 days of culture) per mouse were transplanted into the mice having the above disease and the functionality of the mesenchymal stem cells was estimated for 8 weeks and the results were shown in FIG. 9.

Figure 9A:
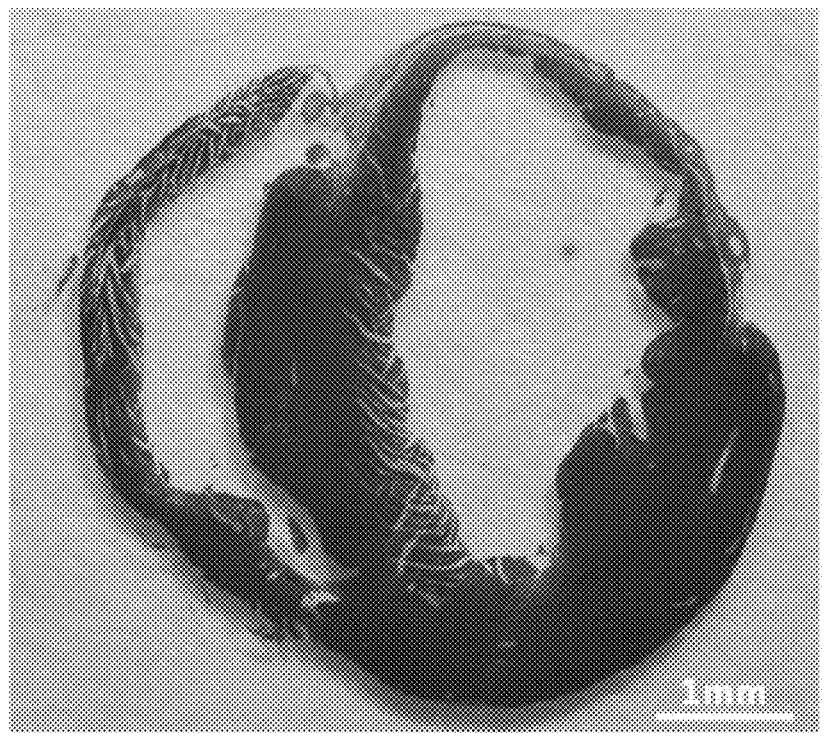
Figure 9B:
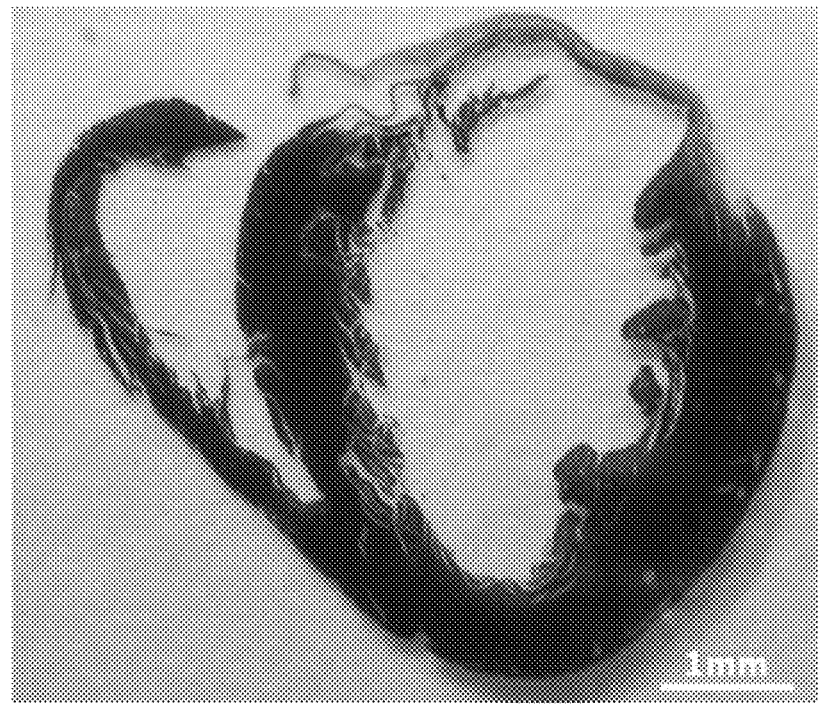
Figure 9C:
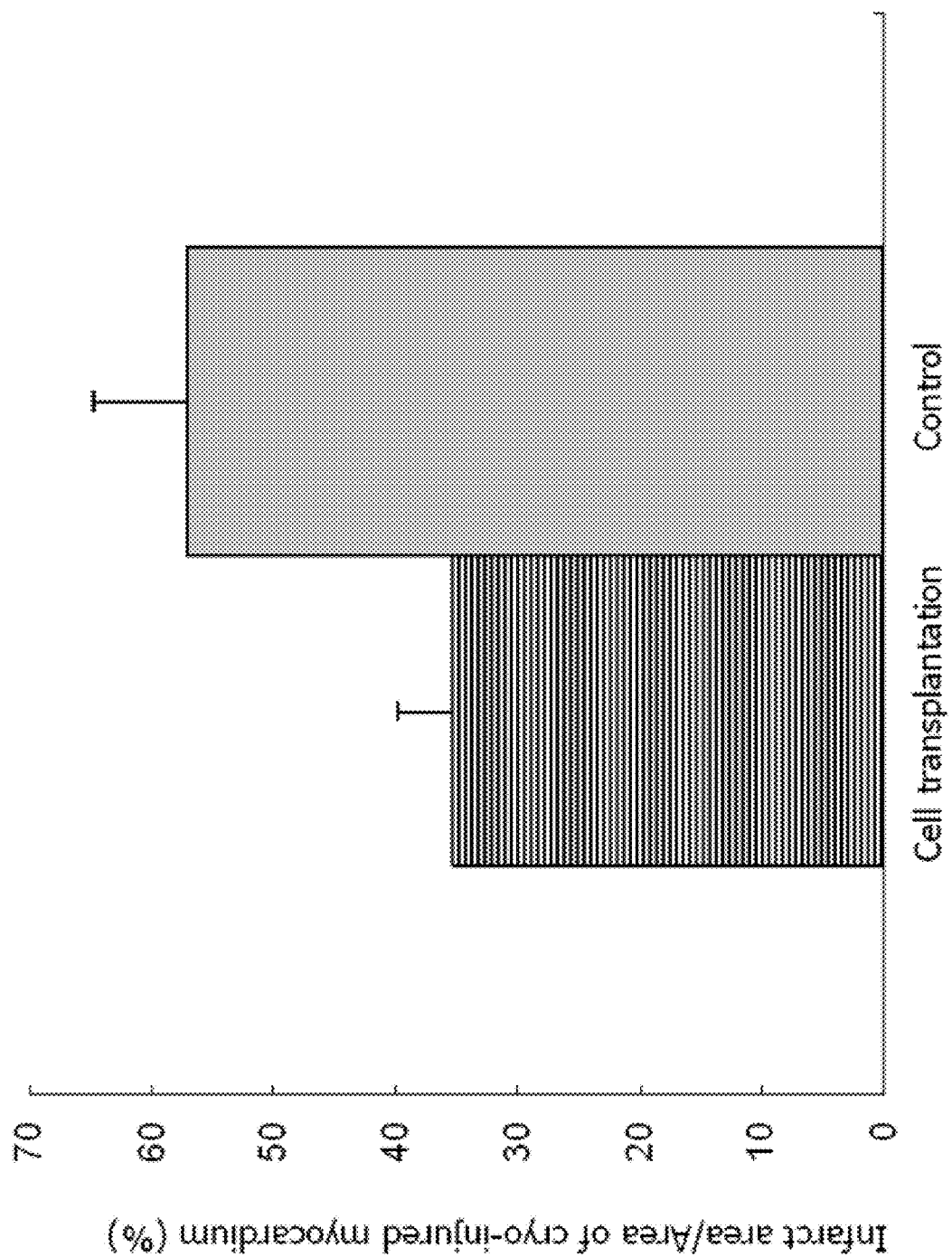

FIGS. 9A and 9B show heart into which the mesenchymal stem cells were transplanted and heat into which the mesenchymal stem cells were not transplanted. Fibrosis was visualized through MT staining, and a blue portion in the drawing indicates fibrosis. It is shown in FIGS. 9A and 9B, that thinning due to fibrosis of cardiac walls was less in a cardiac tissue into which the cells were transplanted (FIG. 9A) than in a cardiac tissue into which the cells were not transplanted (FIG. 9A). That is to say, fibrosis of cardiac walls occurs in the ischemic cardiac disease, and thus, the walls become thinned. Whereas, when the mesenchymal stem cells of the present invention were transplanted, the thinning of the cardiac walls due to fibrosis can be prevented. In addition, FIG. 9C shows results that the fibrosis portion of the cardiac wall in the injury induced area was numerically expressed and quantified, and it is clearly shown that the fibrosis portion is further reduced in a cell transplantation group than in the control without cell transplantation. FIG. 9D shows Echo electrocardiogram measurement results in the 8-week follow-up. Two electrocardiogram measurement records at the $4^{th}$ week and $8^{th}$ week can confirm that movement of the cardiac wall was better in the cell transplantation group than in the control. LVEDD represents diastole, and LVFS represents systole, and as the LVEDD value is smaller and the LVFS value is larger, the cardiac function is better.

It was confirmed from the results, that, when the mesenchymal stem cells of the present invention were transplanted in the ischemic cardiovascular disease model, the cardiac wall does not become thinned, and the mesenchymal stem cells substitute dead tissues, and thus, the fibrosis area causing cardiac malfunction is reduced, thereby finally improving the ischemic cardiovascular disease.

(6) Experiments of Functionality as Autologous Feeders

The possibility that the mesenchymal stem cells of the present invention obtained in Example 1 are usable as feeders for maintaining the human pluripotent stem cells in an undifferentiated state was investigated. In the present experiment, culture was conducted without bFGF, which is an undifferentiated state-maintaining, factor, of the human pluripotent stem cells.

Specifically, human embryonic stem cell line No. 3 of Seoul National University Hospital (SNUhES3) was cultured by using mesenchymal stem cells (SNU3MSC-1) according to the present invention obtained by inducing differentiation of human embryonic stem cell line No. 3 at Seoul National University Hospital (SNUhES3) as feeders. It was confirmed that, when the human embryonic stem cells were cultured without the undifferentiated state-maintaining factor, bFGF, the undifferentiated state of the human embryonic stem cells was maintained in spite of 30 or more passaged cultures (see, FIG. 10). It can be seen from FIG. 10 that, OCT-4, SSEA-4, and TRA-1-60, which are the human pluripotent stem cell markers, were expressed even after 30 passaged cultures, and this proves that undifferentiation capability thereof is intactly maintained. In conclusion, it was confirmed that, when the mesenchymal stem cells of the present invention are used as autologous feeders at the time of culturing of the human pluripotent stem cells, undifferentiation capability of the pluripotent stem cells can be continuously maintained even without addition of bFGF, which was needed for maintaining undifferentiation capability of the pluripotent stem cells during existing culture thereof.

Example 3

Production of Mesenchymal Stem Cells from Human Embryonic Stem Cells of Cha Medical Center and H9 Human Embryonic Stem Cells and Characterization Thereof Conducted were experiments for confirming whether or not the production method of the mesenchymal stem cells of the present invention can be generally applied to human pluripotent stem cells having different genetic backgrounds and/or culture environments, that is, reproducibility thereof. The experiment was conducted by the same method as Example 1 of the present invention, except that human embryonic stem cell line No. 3 of Cha Medical Center (CHA3-hESC) and H9 human embryonic stem cells, which have different genetic backgrounds and/or culture environments from the human embryonic stem cells of Seoul National University Hospital, were used. Specifically, after attachment of the embryonic bodies on day 14 of the culture, spontaneous differentiation into the mesenchymal stem cells is induced in a general culture medium without external addition of cytokine, and then, the mesenchymal stem cells were obtained through maintaining and proliferative culturing using the EGM-2MV medium.

FIG. 11 shows verification results on reproducibility in the production method of the mesenchymal stem cells of the present invention by using human embryonic stem cell line No. 3 of Cha Medical Center (CHA3-hESC) and H9 human embryonic stem cells, which have different genetic backgrounds and/or culture environments from the human embryonic stem cells of Seoul National University Hospital.

Figure 11A:
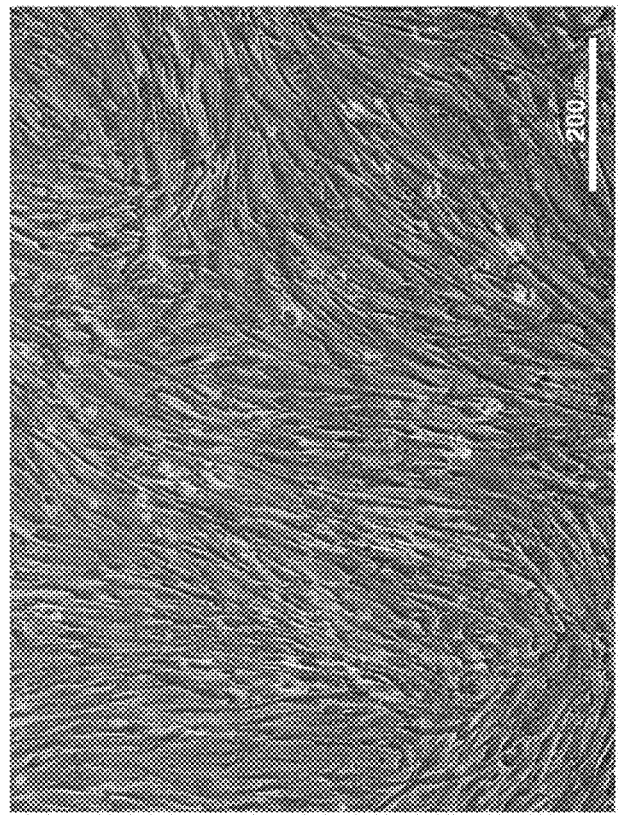
FIG. 11A-F shows verification results on reproducibility of the present invention by using human embryonic stem cell line No. 3 of Cha Medical Center (CHA3-hESC) and H9 human embryonic stem cell line, which have different genetic backgrounds and culture environments from the human embryonic stem cells of Seoul National University Hospital.
Figure 11B:
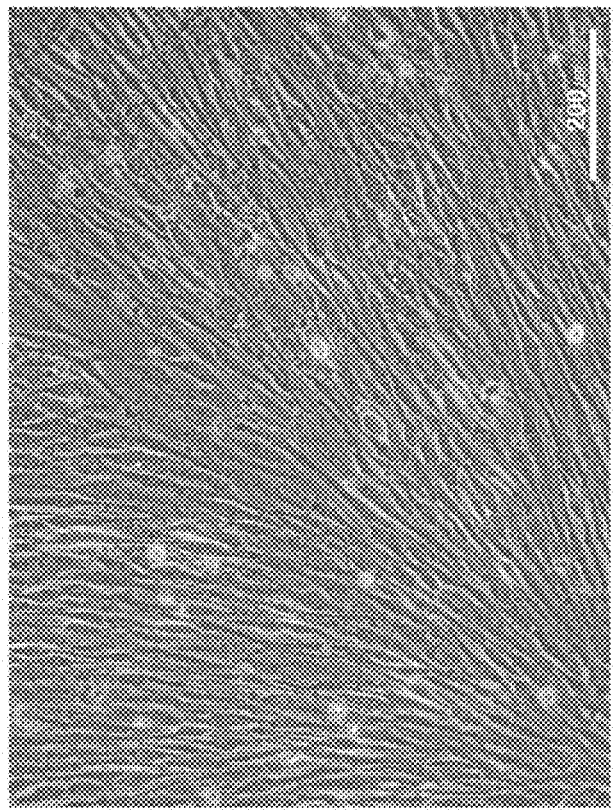
Figure 11C:
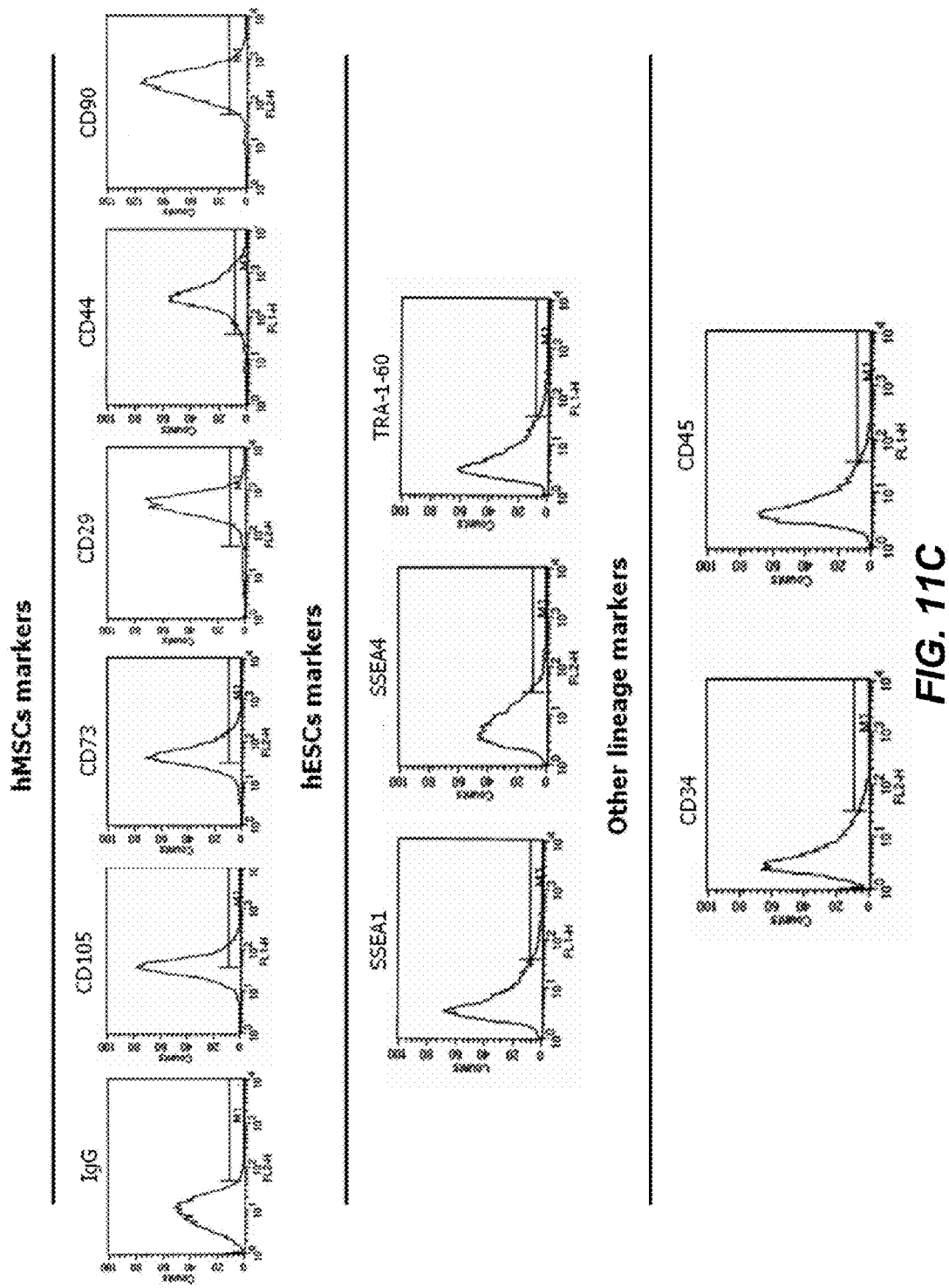
Figure 11D:
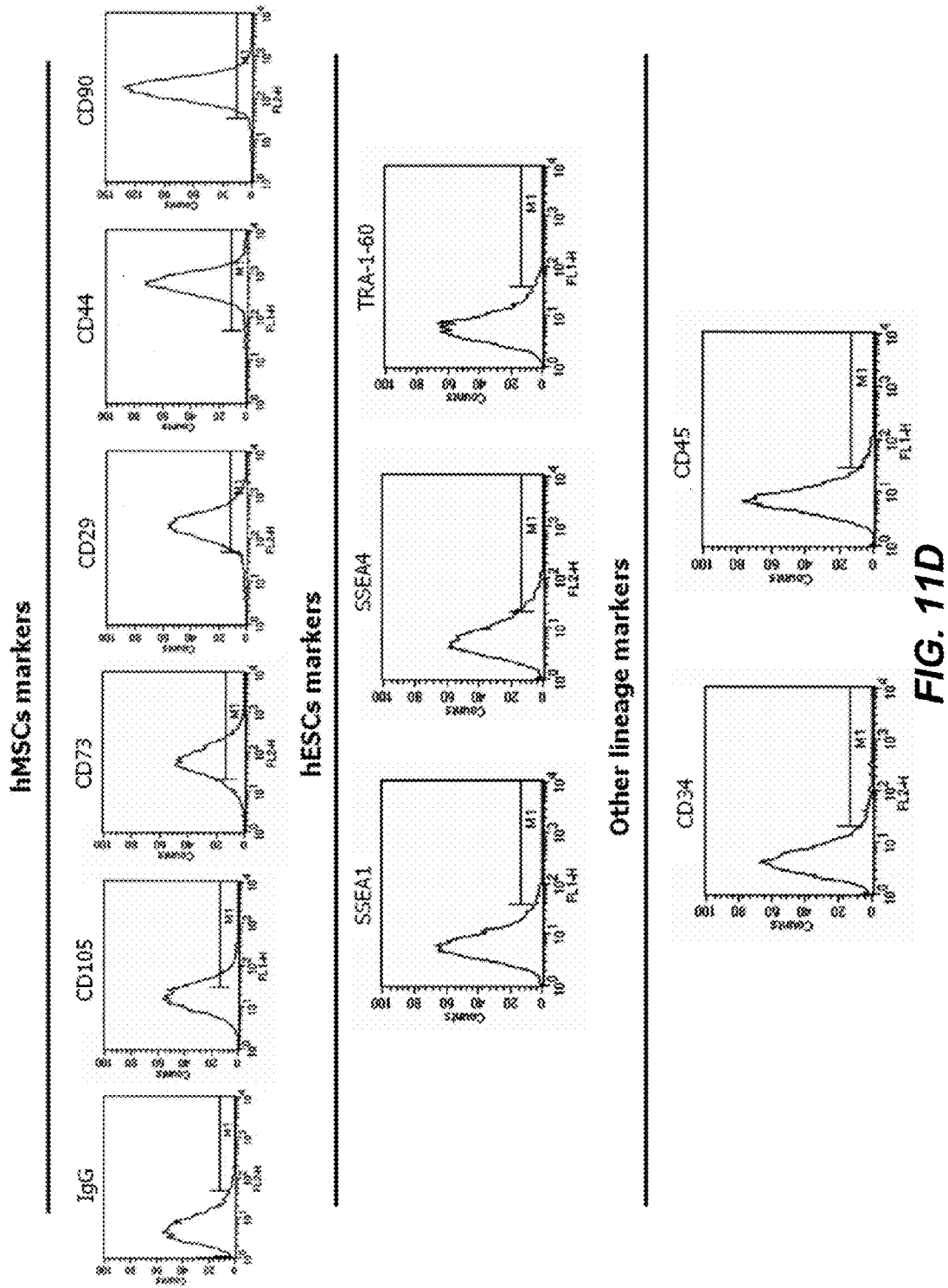
Figure 11E:
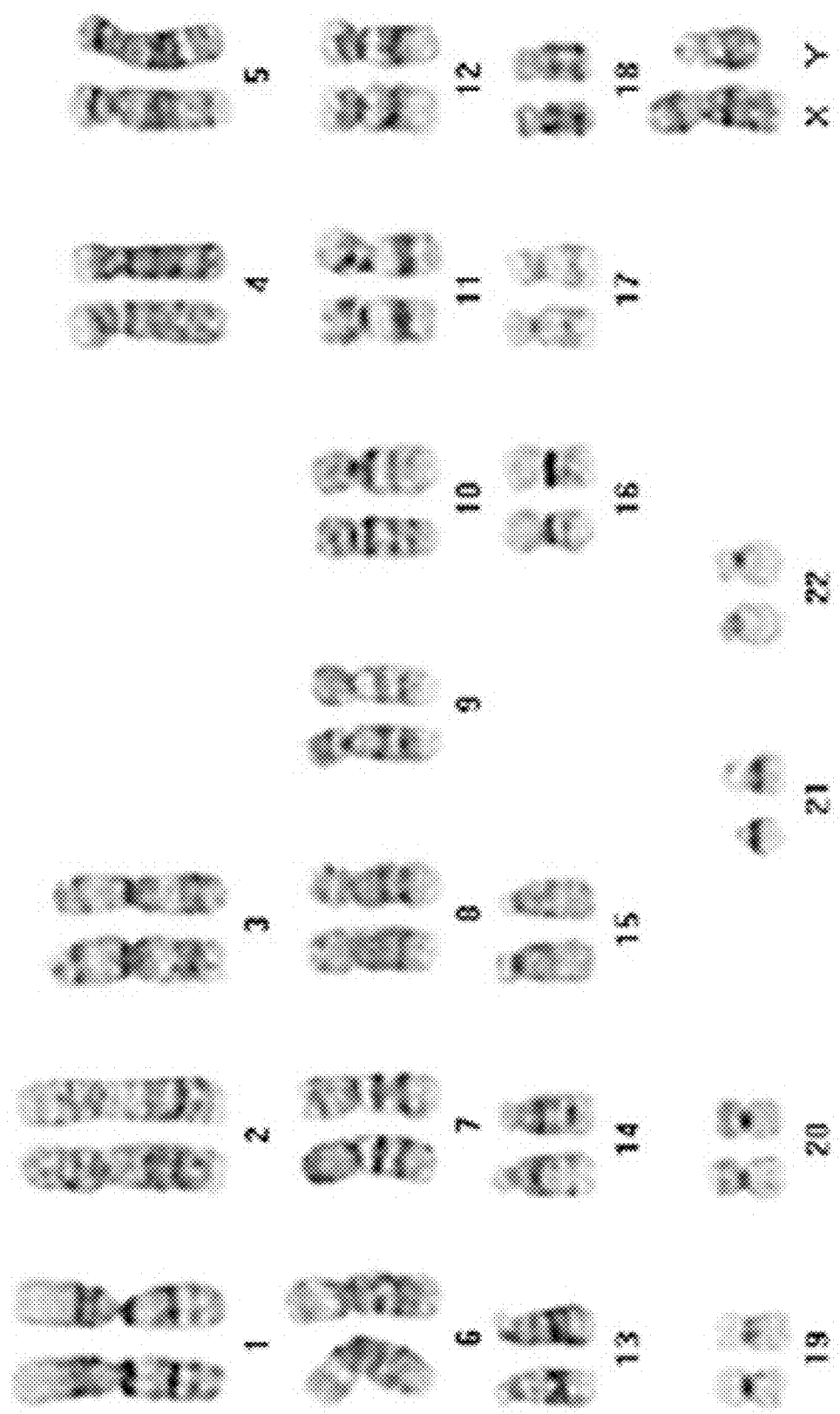
Figure 11F:
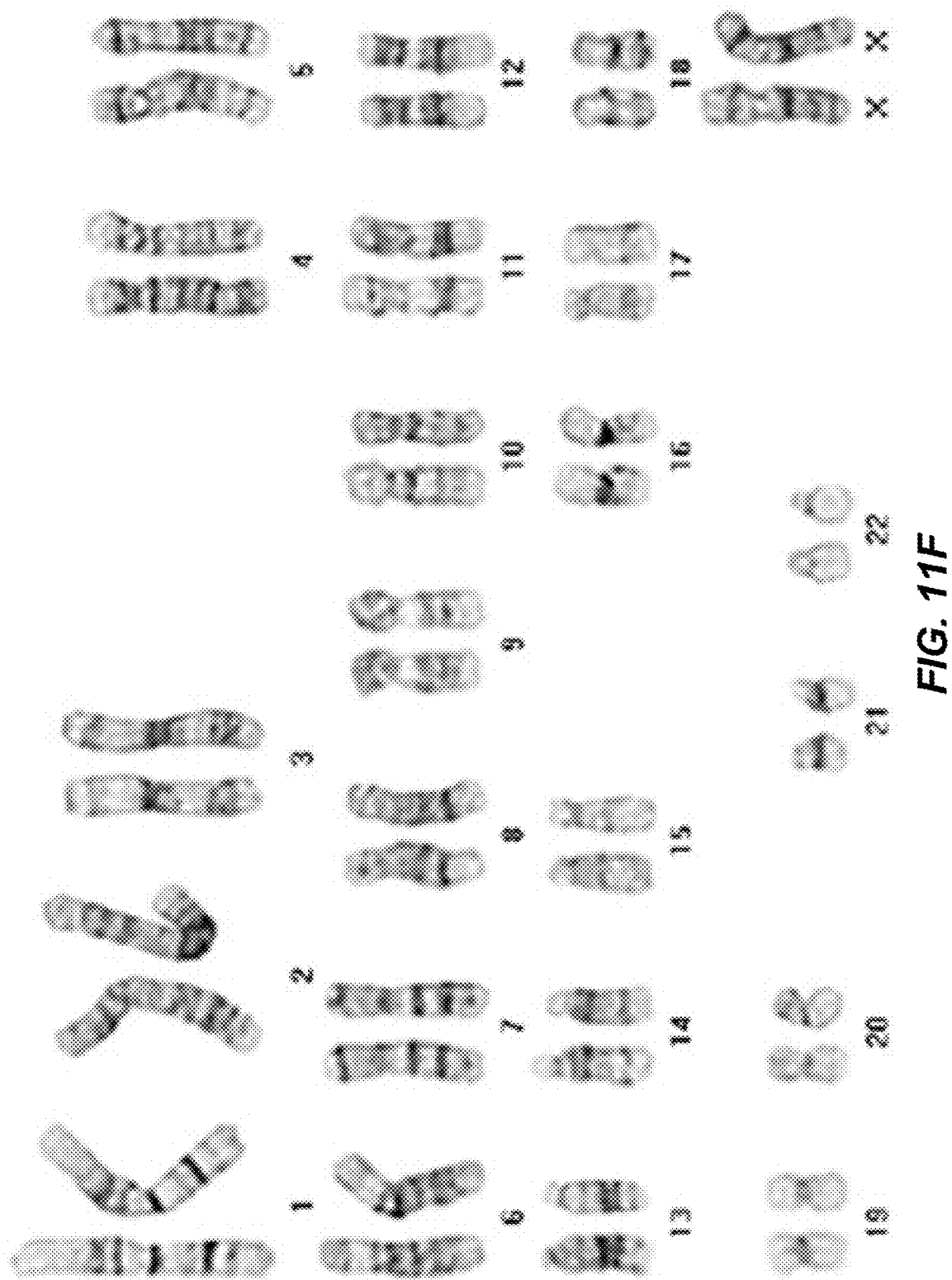

As can be seen from FIG. 11A and FIG. 11B, both the mesenchymal stem cells derived from Cha Medical Center (on day 90 of the culture) and the mesenchymal stem cells derived from H9 cells (on day 90 of the culture) exhibited typical phenotypes of the mesenchymal stem cells. In addition, analysis results of protein expression by using a fluorescent activated cell sorter confirmed that CD105, CD73, CD29, CD44, and CD90, which are protein specific to the mesenchymal stem cells, were recognized as being positive, and SSEA-1, SSEA-4, and TRA-1-60, which are specific markers to the embryonic stem cells, and CD45, CD34, which are markers derived from other germ layers, were recognized as being negative [see, FIG. 11C (D90, mesenchymal stem cells derived from cells of Cha Medical Center and FIG. 11 (D90, mesenchymal stem cells derived from H9 cells)].

In addition, as analysis results of karyotypes of the mesenchymal stem cells, derived from cells of Cha Medical Center (on day 90 of the culture) and the mesenchymal stem cells derived from H9 cells (on day 90 of the culture) by using a G-banding method (Saccone et al., Proc. Natl. Acad. Sci. USA, 89:4913-4917, 1992), it was confirmed that they both had a normal karyotype of XY+44 (see, FIG. 11E and FIG. 11F, respectively).

From the above results, the method of producing mesenchymal stem cells from human pluripotent stem cells according to the present invention was proved to be a standardized method of culturing mesenchymal stem cells, which can be generally applied to human pluripotent stem cells having different genetic backgrounds and/or culture environments.

The present invention provides a standardized method for inducing differentiation and proliferatively culturing of mesenchymal stem cells, which can be broadly applied to all human pluripotent stem cells regardless of a difference in the genetic background thereof. Further, the present invention can continuously mass-produce the mesenchymal stem cells, as the best resources for the cell therapy products, while still maintaining the identity of the mesenchymal stem cells. Further, the present invention can overcome the risk of xeno pathogen due to induction of xeno feeders and cell damage which may result from a sorting by a fluorescent activated cell sorter (FACS), and allow high-efficiency production of the mesenchymal stem cells at low costs. Ultimately, the present invention can easily mass-produce the mesenchymal stem cells, which are ideally usable in regenerative medicine and cell therapy, by using human pluripotent stem cells, thereby realizing practical uses of cell therapy products. Furthermore, the present invention is expected to highly contribute to treatments of incurable diseases, such as cardiovascular diseases and neurological disorders.

According to the present invention, the mesenchymal stem cells can be mass-produced as the best resources for the cell therapy products at low costs, while still maintaining the identity thereof. Ultimately, the present invention can easily mass-produce the mesenchymal stem cells, which can be used ideally in generative medicine and cell therapy, by using human pluripotent stem cells, thereby realizing practical uses of cell treatment agents. Furthermore, the present invention can highly contribute to the treatments of incurable diseases, such as cardiovascular diseases and neurological disorders.

What is claimed is:

1. A method for producing mesenchymal stem cells from human pluripotent stem cells, the method comprising:
    a) culturing the human pluripotent stem cells in an embryonic stem cell culture medium free from bFGF for 14 days to form embryonic bodies, wherein the embryonic body cells express one or more marker(s) selected from brachyury, BMPR, and Sox17;
    b) attaching the embryonic bodies of step a) to a culture dish and culturing the embryonic bodies comprised of embryonic body cells in Dulbecco's Modified Eagle's Medium (DMEM) containing fetal bovine serum (FBS) to induce differentiation of the embryonic body cells into mesenchymal stem cells; and
    c) maintaining and culturing the mesenchymal stem cells of step b) using a culture medium containing human epidermal growth factor (hEGF), vascular endothelial growth factor (VEGF), human fibroblast growth factor-basic (hFGF-B), insulin-like growth factor (IGF-1), hydrocortisone, and ascorbic acid,
    wherein the mesenchymal stem cells of steps b) and c) express one or more markers selected from the group consisting of CD29, CD44, CD73, CD90 and CD105, and
    wherein the mesenchymal stem cells of step c) are capable of being differentiated into cells selected from the group consisting of adipocytes, osteocytes, chondrocytes, myocytes, neurocytes, and cardiomyocytes.

2. The method of claim 1, wherein the mesenchymal stem cells phenotype comprises CD29(+), CD44(+), CD73(+), CD90(+), CD105(+), SSEA-1(−), SSEA-4(−), TRA-1-60(−), CD45(−), and CD34(−).

* * * * *